United States Patent
Kang et al.

(10) Patent No.: US 11,225,472 B2
(45) Date of Patent: Jan. 18, 2022

(54) PHENYL PROPIONIC ACID DERIVATIVES AND USES THEREOF

(71) Applicant: IL DONG PHARMACEUTICAL CO., LTD., Seoul (KR)

(72) Inventors: Jae-Hoon Kang, Seoul (KR); Hong-Sub Lee, Gyeonggi-do (KR); Kyung-Mi An, Gyeonggi-do (KR); Chang-Hee Hong, Seoul (KR); Hyun-Jung Kwak, Gyeonggi-do (KR); Shuo-Lin Cui, Gyeonggi-do (KR); Hyo-Jung Song, Seoul (KR)

(73) Assignee: IL DONG PHARMACEUTICAL CO., LTD.

( * ) Notice: Subject to any disclaimer, the term of this patent is extended or adjusted under 35 U.S.C. 154(b) by 0 days.

(21) Appl. No.: 16/467,654

(22) PCT Filed: Dec. 14, 2017

(86) PCT No.: PCT/KR2017/014757
§ 371 (c)(1),
(2) Date: Jun. 7, 2019

(87) PCT Pub. No.: WO2018/111012
PCT Pub. Date: Jun. 21, 2018

(65) Prior Publication Data
US 2020/0223833 A1    Jul. 16, 2020

(30) Foreign Application Priority Data
Dec. 15, 2016 (KR) .................. 10-2016-0171541
Dec. 13, 2017 (KR) .................. 10-2017-0171228

(51) Int. Cl.
*C07D 409/12* (2006.01)
*C07D 405/12* (2006.01)
*A61P 3/04* (2006.01)
*A61P 3/10* (2006.01)
*C07D 405/14* (2006.01)

(52) U.S. Cl.
CPC .............. *C07D 409/12* (2013.01); *A61P 3/04* (2018.01); *A61P 3/10* (2018.01); *C07D 405/12* (2013.01); *C07D 405/14* (2013.01)

(58) Field of Classification Search
CPC .. C07D 409/12; C07D 405/12; C07D 405/14; A61P 3/04
USPC ........................................................ 514/333
See application file for complete search history.

(56) References Cited

FOREIGN PATENT DOCUMENTS

| JP | 2015523339 | 8/2015 |
|---|---|---|
| WO | 2005/086661 A2 | 9/2005 |
| WO | 2005087710 | 9/2005 |
| WO | 2006/130707 A2 | 12/2006 |
| WO | 2007/033002 A1 | 3/2007 |
| WO | WO-2007033002 A1 * | 3/2007 ........... C07D 257/04 |
| WO | 2017180457 A1 | 10/2017 |

OTHER PUBLICATIONS

Gowhar Ali et al. Input of Isosteric and Bioisosteric Approach in Drug Design. (Year: 2013).*
Latour et al., "GPR40 is Necessary but Not Sufficient for Fatty Acid Stimulation of Insulin Secretion In Vivo," Diabetes, 2007, 56:1087-1094.
Nagasumi et al., "Overexpression of GPR40 in Pancreatic Beta-Cells Augments Glucose-Stimulated Insulin Secretion and Improves Glucose Tolerance in Normal and Diabetic Mice," Diabetes, 2009, 58:1067-1076.
Verma et al., "Activation of GPR40 attenuates chronic inflammation induced impact on pancreatic β-cells health and function," BMC Cell Biol., 2014, 15:24.
Kaku et al., "Efficacy and safety of fasiglifam (TAK-875), a G protein-coupled receptor 40 agonist, in Japanese patients with type 2 diabetes inadequately controlled by diet and exercise: a randomized, double-blind, placebo-controlled, phase III trial," Diabetes obes metab., 2015, 17:675-681.
Houze et al., "AMG 837: A potent, orally bioavailable GPR40 agonist," Bioorganic & Medicinal Chemistry Letters, 2012, vol. 22, pp. 1267-1270.
Yao et al., "An efficient multistep ligand-based virtual screening approach for GPR40 agonists," Molecular Diversity, 2014, vol. 18, pp. 183-193.
Walsh et al., "3-Substituted 3-(4-aryloxyaryl)-propanoic acids as GPR40 agonists," Bioorganic & Medicinal Chemistry Letters, 2011, vol. 21, pp. 3390-3394.
S. Agarwal, et al., "Identification of an Orally Efficacious GPR40/FFAR1 Receptor Agonist", ACS Medicinal Chemistry Letters, Dec. 2016 (Dec. 8, 2016), 7: 1314-1138.
First Examination Report for New Zealand App. No. 753053, dated Feb. 7, 2020, 5 pages.

* cited by examiner

*Primary Examiner* — Rita J Desai
(74) *Attorney, Agent, or Firm* — Riverside Law LLP

(57) ABSTRACT

The present invention relates to the compounds according to Formula (I), the racemates, enantiomers, diastereomers thereof or pharmaceutical acceptable salts thereof, or pharmaceutical compositions comprising these, for the treatment or prevention of metabolic disorders. The compounds according to Formula (I) are, as GPR40 agonists, available for oral administration with glucose-dependent insulin secretion mechanism, which exhibit excellent glucose lowering efficacy without the risk of hypoglycemia. Thus, the compounds and/or pharmaceutical compositions comprising the compounds as effective components are useful in treating and/or preventing symptoms of type 2 diabetes through adequate control of blood glucose.

17 Claims, No Drawings

PHENYL PROPIONIC ACID DERIVATIVES AND USES THEREOF

CROSS-REFERENCE TO RELATED APPLICATIONS

This application is the U.S. national phase application filed under 35 U.S.C. § 371 claiming benefit to International Patent Application No. PCT/KR2017/014757, filed on Dec. 14, 2017, which is entitled to priority under to Korean Patent Application No. 10-2016-0171541, filed Dec. 15, 2016 and Korean Patent Application No. 10-2017-0171228, filed Dec. 13, 2017, the disclosure of which is incorporated herein by reference in its entirety.

TECHNICAL FIELD

The present invention relates to phenyl propionic acid derivatives, isomers, and pharmaceutically permissible salts thereof, and on its medicinal uses.

BACKGROUND ART

Diabetes mellitus (DM) is mainly divided into Type 1 and Type 2 diabetes. Type 1 diabetes mellitus (T1DM) is a condition characterized by the genetically predisposed destruction of pancreatic β-cells that are responsible for the production of insulin, which results in the body's inability to produce sufficient insulin for the control of blood glucose level. Type 2 diabetes mellitus (T2DM), covering up to 95% of the total diabetic patients, is an acquired disease in which environmental factors cause somatic cells to become insulin-resistant, which in terms disables effective absorption of blood glucose. Chronic rise in blood glucose level caused by insulin abnormality leads to serious complications, including obesity, neuralgia, diabetic retinopathy, nephropathy, cardiovascular diseases and dyslipidemia.

Early symptoms of onset of the disease include hyperuresis and unidentified weight loss, and the disease itself can be properly diagnosed through precise examinations of HbA1c level, fasting and postprandial glucose level, and glucose tolerance test. T2DM patients generally display HbA1c level of over 6.5%, fasting plasma glucose (FPG after 8 hrs) level of over 126 mg/dL, and the postprandial level (2 hrs-Plasma Glucose) of over 200 mg/dL. According to data from the International Diabetes Federation (IDF), the number of T2DM patients around the globe increased from 30 million in 1985 to 415 million in 2015, and is expected to rise by 7 million annually to 642 million adult patients by 2040, which marks over 10% of the global population. In addition, approximately 50% of the patients also suffer from related complications with 5 million resulting deaths, making them responsible for 14.5% of the global death count.

Increasing number of patients has resulted in subsequent growth of the global market for the treatment of T2DM. The market value increased significantly from 28.8 billion dollars in 2009 to 63.6 billion dollars in 2014 and is expected to reach 163.2 billion dollars by 2020. Dietary habits, lack of exercise and irregular lifestyle have been pointed out as the indirect causes of such increase in the occurrence of diabetes mellitus. Therefore, patients are prescribed a variety of medicinal treatments along with balanced diet, regular exercise and maintenance of healthy weight, but there still are unmet needs for discovery of novel medications for the full recovery of the disease.

Currently being actively prescribed medications for T2DM can be categorized based on their mechanisms of action. However, each type has shortcomings which cannot be overcome. For example, Metformin of biguanide type, the primary treatment for T2DM, places patients at risk of diarrhea, abdominalgia, dyspepsia, and lack of durability in long-term use. Sulfonylureas (SUs), independent from blood glucose level, stimulate pancreatic β-cells and thus place patients at risk of hypoglycemia. Liver safety concerns, CV risk, weight gain and risk of bladder cancer have been reported with thiazolidinediones, so the drug has been withdrawn from the market. Sodium-glucose co-transporter-2 (SGLT-2) inhibitors make patients become vulnerable to urinary tract and genital infections, and α-glucosidase inhibitors may induce side-effects including dyspepsia and diarrhea. Furthermore, Dipeptidyl peptidase-4 (DPP-IV) inhibitors are limited to patients without any renal conditions. Therefore, there is a need for discovery of novel medications for T2DM which is able to overcome such limitations, and accordingly, GPR40 (G-protein-coupled receptor 40) agonists have recently been gaining attention.

G-protein coupled receptor 40 (GPR40), a seven-transmembrane protein, is a type of GPCR of the rhodopsin family, and is primarily expressed in β-cells of pancreatic islets. Since its primary ligands are medium-to-long change fatty acids, the receptor is also known as Free fatty acid receptor 1 (FFAR1).

The mechanism of pancreatic β-cell's insulin secretion through GPR40 is mainly determined by either ligands or GPR40 agonists that bind to the receptor. When binding activates the receptor, primary signaling pathway for insulin secretion is promoted through $G\alpha_{q/11}$, which is a type of subunits of GPCR. Then, the pathway hydrolyzes cell membrane phospholipids through Phospholipase C (PLC) to produce Diacyglyceral (DAG) and Inositol trisphosphate ($IP_3$), which subsequently activate Protein Kinase D1 (PKD1) to induce F-actin protein modification, and Calcium ion secretion to ultimately induce insulin secretion.

The mechanism that GPR40 activation induces insulin secretion with blood glucose-dependent manner was proven through experiments using rodent models. (Diabetes, 2007, 56, 1087-1094; Diabetes, 2009, 58, 1067-1076). Such blood glucose-dependent mechanism of insulin secretion has no risk of hypothermia, which makes GPR40 an attractive target for novel drug development. In addition, GPR40 is involved in maintaining pancreatic β-cell survival through regulation of PIX-1 and BCL2, which also results in sustaining of efficacy even in a long-term treatment (BMC Cell Biol., 2014, 15, 24). Furthermore, since the distribution of GPR40 expression is relatively limited, there is low risk of adverse effects in other organs, and improving blood-glucose homeostasis through GPR40 activation is potentially involved in other metabolic disorders including obesity and hypertension.

Based on such advantages, for the past few years, industrial efforts have made investments in the development of GPR40 agonists, but no drug has been released to the market. Among the discoveries, Fasiglifam of Takeda, the first GPR40 agonist to enter clinical trials, has been shown its glucose-lowering efficacy in patients with T2DM in phase II trials. However, despite its efficacy, the compound was discontinued in phase III trial due to liver safety concerns (Diabetes obes metab., 2015, 17, 675-681).

It is definitive that discovery of novel GPR40 agonists which bear mechanism of glucose-dependent insulin secretion is in necessity of modern society, where the number of patients suffering from metabolic disorders including T2DM is still drastically increasing, to provide effective means of treating such metabolic diseases.

DISCLOSURE

Technical Problem

The objective of the present invention relies on providing agonists acting on GPR40; particularly novel phenyl propionic acid derivatives, isomers, and pharmaceutically available salts thereof.

In addition, the object of the present invention is to provide medicinal use for treatment of GPR40-mediated disorders.

However, the technical object to be achieved in the present invention is not limited to those aforementioned above, and other objects may be clearly understood by those skilled in the art from the following description.

Technical Solution

Compounds represented by Formula (I); a racemate, an enantiomer, or a diastereomer thereof, or a pharmaceutically acceptable salt thereof:

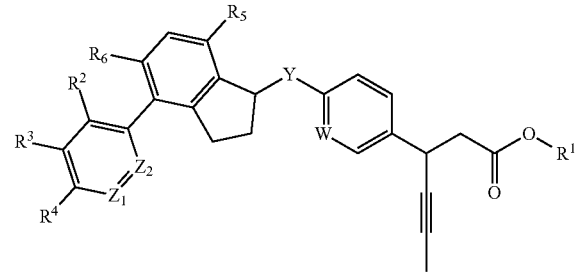

[Formula (I)]

$R^1$ is hydrogen, or $C_{1-4}$ linear or branched alkyl;
$R^2$ is hydrogen, cyano, hydroxyl, $C_{1-4}$ linear or branched alkyl, or $C_{1-4}$ linear or branched alkoxy;
$R^3$ and $R^4$ are each independently hydrogen, halogen, cyano, $C_{1-4}$ linear or branched alkoxy, or $OR^8$;
wherein $R^8$ is hydrogen; $C_{3-10}$ heterocycloalkyl comprising 1-4 hetero atoms selected from the group consisting of N, O, and S; or substituted alkyl with $C_{3-10}$ heterocycloalkyl comprising 1-4 hetero atoms selected from the group consisting of N, O, and S;
$R^5$ and $R^6$ are each independently hydrogen, halogen, cyano, halomethyl, hydroxyl, $C_{1-4}$ linear or branched alkyl, or $C_{1-4}$ linear or branched alkoxy;
Y is NH or O;
$Z^1$, $Z^2$ and W are each independently $CR^7$ or N;
wherein $R^7$ is hydrogen, halogen, cyano, hydroxyl, $C_{1-4}$ linear or branched alkyl, or $C_{1-4}$ linear or branched alkoxy.

This invention is provided to the compounds according to Formula (I), as racemates, enantiomers, diastereomers thereof; or pharmaceutical acceptable salts, for the treatment of disorders; wherein responsive to agonism of the GPR40.

This invention is provide to the process of compounds according to Formula (I), as racemates, enantiomers, diasteromers thereof; or pharmaceutical acceptable salts.

Advantageous Effects

The compounds of the present invention, as GPR40 agonists, are orally available and are extremely effective in lowering blood glucose level to normal state without any risk of inducing hypoglycemia via glucose-dependent insulin secretion. Therefore, compounds and/or therapeutically effective pharmaceutical composition comprising the compounds of the present invention are useful in the treatment, delaying, and/or regression of symptoms of type 2 diabetes. In addition, compounds of the present invention modulate glucose excursion via GPR40 activation; the therapeutic effect can also be potentially available in obesity and hypertension.

In addition, since the compounds of the present invention have shown improved and/or enhanced therapeutic effects of alleviating and/or treating symptoms of type 2 diabetes compared to pre-existing medications when evaluated of glucose-lowering effects of the compounds on animal models and/or human-organ derived materials, the compounds can be evaluated as being highly useful to potential beneficiaries of the present invention.

Mode for Invention

Compounds represented by Formula (I); a racemate, an enantiomer, or a diastereomer thereof, or a pharmaceutically acceptable salt thereof:

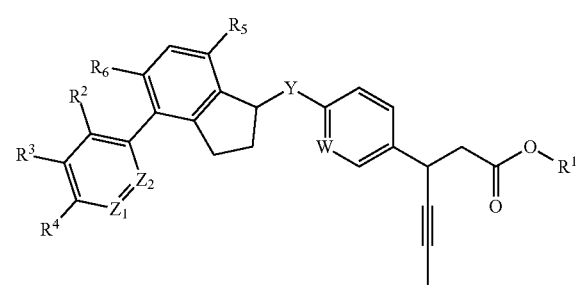

[Formula (I)]

$R^1$ is hydrogen, or $C_{1-4}$ linear or branched alkyl;
$R^2$ is hydrogen, cyano, hydroxyl, $C_{1-4}$ linear or branched alkyl, or $C_{1-4}$ linear or branched alkoxy;
$R^3$ and $R^4$ are each independently hydrogen, halogen, cyano, $C_{1-4}$ linear or branched alkoxy, or $OR^8$;
wherein $R^8$ is hydrogen; $C_{3-10}$ heterocycloalkyl comprising 1-4 hetero atoms selected from the group consisting of N, O, and S; or substituted alkyl with $C_{3-10}$ heterocycloalkyl comprising 1-4 hetero atoms selected from the group consisting of N, O, and S;
$R^5$ and $R^6$ are each independently hydrogen, halogen, cyano, halomethyl, hydroxyl, $C_{1-4}$ linear or branched alkyl, or $C_{1-4}$ linear or branched alkoxy;
Y is NH or O;
$Z^1$, $Z^2$ and W are each independently $CR^7$ or N;
wherein $R^7$ is hydrogen, halogen, cyano, hydroxyl, $C_{1-4}$ linear or branched alkyl, or $C_{1-4}$ linear or branched alkoxy.

Examples of preferred compounds according to the Formula (I) in present invention are following:
(S)-3-(4-(((R)-4-(6-((1,1-dioxidotetrahydro-2H-thiopyran-4-yl)oxy)pyridin-3-yl)-7-fluoro-2,3-dihydro-1H-inden-1-yl)oxy)phenyl)hex-4-ynoic acid;
(S)-3-(4-(((R)-7-fluoro-4-(6-((3-methyloxetan-3-yl)methoxy)pyridin-3-yl)-2,3-dihydro-1H-inden-1-yl)oxy)phenyl)hex-4-ynoic acid;
(S)-3-(4-(((R)-4-(6-(2-(1,1-dioxidothiomorpholino)ethoxy)pyridin-3-yl)-7-fluoro-2,3-dihydro-1H-inden-1-yl)oxy)phenyl)hex-4-ynoic acid;

(S)-3-(4-(((R)-7-fluoro-4-(6-(oxetan-3-yloxy)pyridin-3-yl)-2,3-dihydro-1H-inden-1-yl)oxy)phenyl)hex-4-ynoic acid;

(S)-3-(4-(((R)-7-fluoro-4-(6-(((R)-tetrahydrofuran-3-yl)oxy)pyridin-3-yl)-2,3-dihydro-1H-inden-1-yl)oxy)phenyl)hex-4-ynoic acid;

(S)-3-(4-(((R)-7-fluoro-4-(6-((tetrahydro-2H-pyran-4-yl)oxy)pyridin-3-yl)-2,3-dihydro-1H-inden-1-yl)oxy)phenyl)hex-4-ynoic acid;

(S)-3-(4-(((R)-7-fluoro-4-(6-MS)-tetrahydrofuran-3-yl)oxy)pyridin-3-yl)-2,3-dihydro-1H-inden-1-yl)oxy)phenyl)hex-4-ynoic acid;

(S)-3-(4-(((R)-7-fluoro-4-(4-methyl-6-(((R)-tetrahydrofuran-3-yl)oxy)pyridin-3-yl)-2,3-dihydro-1H-inden-1-yl)oxy)phenyl)hex-4-ynoic acid;

(S)-3-(4-(((R)-7-fluoro-4-(2-methyl-6-(((R)-tetrahydrofuran-3-yl)oxy)pyridin-3-yl)-2,3-dihydro-1H-inden-1-yl)oxy)phenyl)hex-4-ynoic acid;

(S)-3-(4-(((R)-4-(5-chloro-6-(((R)-tetrahydrofuran-3-yl)oxy)pyridin-3-yl)-7-fluoro-2,3-dihydro-1H-inden-1-yl)oxy)phenyl)hex-4-ynoic acid;

(S)-3-(4-(((R)-7-fluoro-4-(5-(((R)-tetrahydrofuran-3-yl)oxy)pyridin-2-yl)-2,3-dihydro-1H-inden-1-yl)oxy)phenyl)hex-4-ynoic acid;

(S)-3-(4-(((R)-7-fluoro-4-(4-methyl-6-((3-methyloxetan-3-yl)methoxy)pyridin-3-yl)-2,3-dihydro-1H-inden-1-yl)oxy)phenyl)hex-4-ynoic acid;

(S)-3-(4-(((R)-7-fluoro-4-(2-methyl-6-((3-methyloxetan-3-yl)methoxy)pyridin-3-yl)-2,3-dihydro-1H-inden-1-yl)oxy)phenyl)hex-4-ynoic acid;

(S)-3-(4-(((R)-7-fluoro-4-(5-((3-methyloxetan-3-yl)methoxy)pyridin-2-yl)-2,3-dihydro-1H-inden-1-yl)oxy)phenyl)hex-4-ynoic acid;

(S)-3-(4-(((R)-7-fluoro-4-(5-(((R)-tetrahydrofuran-3-yl)oxy)pyridin-3-yl)-2,3-dihydro-1H-inden-1-yl)oxy)phenyl)hex-4-ynoic acid;

(S)-3-(4-(((R)-7-fluoro-4-(5-((tetrahydro-2H-pyran-4-yl)oxy)pyridin-3-yl)-2,3-dihydro-1H-inden-1-yl)oxy)phenyl)hex-4-ynoic acid;

(S)-3-(4-(((R)-4-(5-chloro-6-((tetrahydro-2H-pyran-4-yl)oxy)pyridin-3-yl)-7-fluoro-2,3-dihydro-1H-inden-1-yl)oxy)phenyl)hex-4-ynoic acid;

(S)-3-(4-(((R)-4-(5-cyano-6-(((R)-tetrahydrofuran-3-yl)oxy)pyridin-3-yl)-7-fluoro-2,3-dihydro-1H-inden-1-yl)oxy)phenyl)hex-4-ynoic acid;

(S)-3-(4-(((R)-4-(5-cyano-6-((tetrahydro-2H-pyran-4-yl)oxy)pyridin-3-yl)-7-fluoro-2,3-dihydro-1H-inden-1-yl)oxy)phenyl)hex-4-ynoic acid;

(S)-3-(4-(((R)-5-cyano-4-(6-(((R)-tetrahydrofuran-3-yl)oxy)pyridin-3-yl)-2,3-dihydro-1H-inden-1-yl)oxy)phenyl)hex-4-ynoic acid;

(S)-3-(4-(((R)-5-fluoro-4-(6-(((R)-tetrahydrofuran-3-yl)oxy)pyridin-3-yl)-2,3-dihydro-1H-inden-1-yl)oxy)phenyl)hex-4-ynoic acid;

(S)-3-(4-(((R)-5-methoxy-4-(6-(((R)-tetrahydrofuran-3-yl)oxy)pyridin-3-yl)-2,3-dihydro-1H-inden-1-yl)oxy)phenyl)hex-4-ynoic acid;

(S)-3-(4-(((R)-5-cyano-4-(6-((tetrahydro-2H-pyran-4-yl)oxy)pyridin-3-yl)-2,3-dihydro-1H-inden-1-yl)oxy)phenyl)hex-4-ynoic acid;

(S)-3-(4-(((R)-5-fluoro-4-(6-((tetrahydro-2H-pyran-4-yl)oxy)pyridin-3-yl)-2,3-dihydro-1H-inden-1-yl)oxy)phenyl)hex-4-ynoic acid;

(S)-3-(4-(((R)-5-methoxy-4-(6-((tetrahydro-2H-pyran-4-yl)oxy)pyridin-3-yl)-2,3-dihydro-1H-inden-1-yl)oxy)phenyl)hex-4-ynoic acid;

(S)-3-(4-(((R)-7-fluoro-4-(6-(((R)-tetrahydrofuran-3-yl)oxy)pyridin-3-yl)-2,3-dihydro-1H-inden-1-yl)amino)phenyl)hex-4-ynoic acid;

3-(6-(((R)-7-fluoro-4-(6-(((R)-tetrahydrofuran-3-yl)oxy)pyridin-3-yl)-2,3-dihydro-1H-inden-1-yl)oxy)pyridin-3-yl)hex-4-ynoic acid.

In the present invention, "heterocycloalkyl" refers to cycloalkyl groups containing hetero atoms. Exemplary heterocycloalkyl groups include, but not limited to, oxetane, tetrahydrofuran, pyran, azetidine, pyrrolidinyl, piperazinyl, morpholine or thiomorpholine.

In the present invention, "$C_{1-4}$ alkyl" is a saturated hydroxylcarbonyl group with linear or branched chains of 1 to 4 carbon atoms. Exemplary alkyl groups include, but not limited to, methyl, ethyl, propyl, buthyl, 1-methylethyl, diethyl or dimethyl.

In the present invention, "$C_{1-4}$ alkoxy" is an OR group with 1 to 4 carbon atoms and R as defined above. Exemplary alkoxy groups include, but not limited to, methoxy, ethoxy, propoxy, butoxy, 1-methylethoxy or 1, 1-dimethylethoxy.

In the present invention, "$C_{1-2}$ alkyl" is a saturated hydroxylcarbonyl group with linear or branched chains of 1 to 2 carbon atoms. Exemplary alkyl groups include, but not limited to, methyl or ethyl.

In the present invention, "$C_{1-2}$ alkoxy" is an OR group with 1 to 2 carbon atoms and R as defined above. Exemplary alkoxy groups include, but not limited to, methoxy or ethoxy.

In the present invention, "halo" is defined as bromine, fluorine, or chlorine atom.

Herein, the term "pharmaceutically acceptable" refers to a usable component or composition, within the medical criteria, that does not incorporate irrational risk of toxicity.

The compounds of the invention contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. A stereoisomer is referred to as an enantiomer, and a mixture of such isomers is often called an enantiomeric mixture. A 50:50 mixture of enantiomers is referred to as a racemic-mixture or a racemate.

In the present invention, "diastereomer" refers to a stereoisomer with two or more centers of chirality and whose molecules are not mirror images of one another. Diastereomers have different physical properties, such as melting points, boiling points, spectral properties, and reactivity. Mixtures of diastereomers may become separated under high resolution analytical procedures such as electrophoresis and chromatography.

In the present invention, "enantiomers" refer to two stereoisomers of a compound which are non-superimposable mirror images of one another.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or methanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminium and lithium.

In another aspect, the present invention provides a method of preparing the compounds represented by Formula (I) or pharmaceutically approved salts thereof.

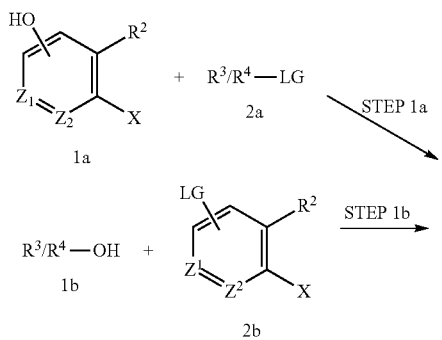

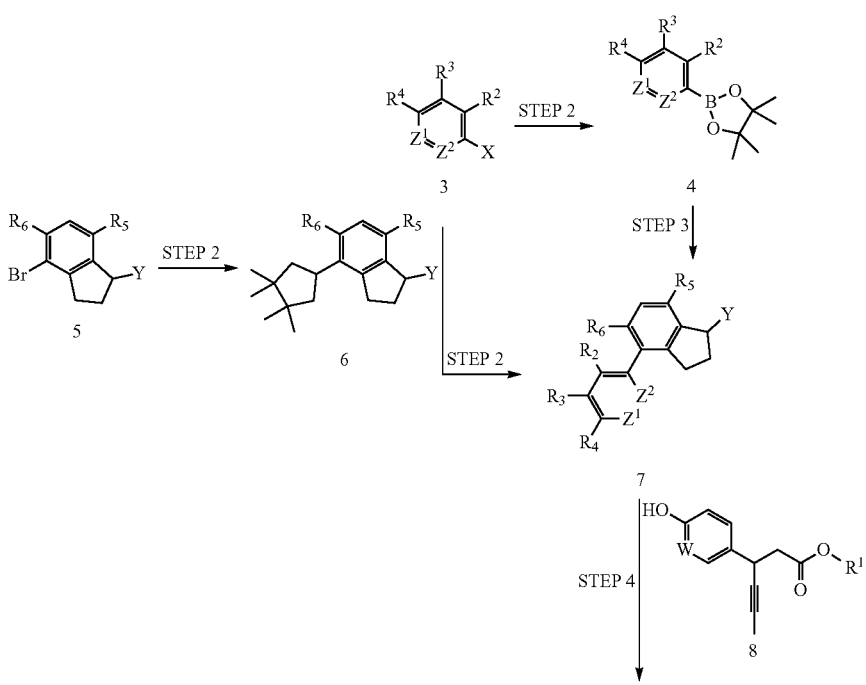

-continued

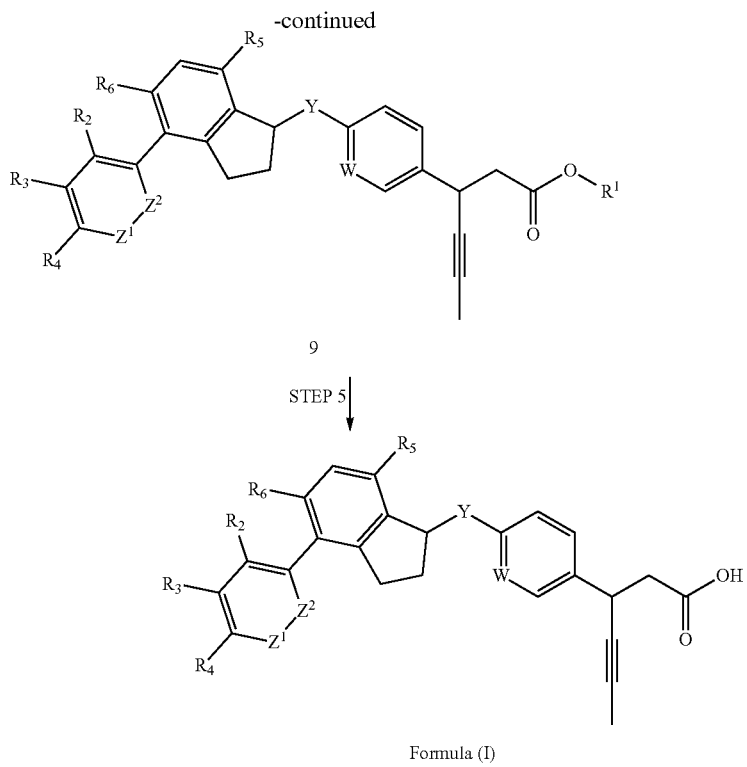

Formula (I)

Unless otherwise stated, the groups, residues, and substituent, particularly $R^6$, Y, W, $Z^1$, and $Z^2$ are defined as above and hereinafter.

*93$R^1$ is hydrogen, or $C_{1-4}$ linear or branched alkyl;

$R^2$ is hydrogen, cyano, hydroxyl, $C_{1-4}$ linear or branched alkyl, or $C_{1-4}$ linear or branched alkoxy;

$R^3$ and $R^4$ are each independently hydrogen, halogen, cyanide, $C_{1-4}$ linear or branched alkoxy, or $OR^8$;

wherein $R^8$ is hydrogen; $C_{3-10}$ heterocycloalkyl comprising 1-4 hetero atoms selected from the group consisting of N, O, and S; or substituted alkyl with $C_{3-10}$ heterocycloalkyl comprising 1-4 hetero atoms selected from the group consisting of N, O, and S;

$R^5$ and $R^6$ are each independently hydrogen, halogen, cyano, halomethyl, hydroxyl, $C_{1-4}$ linear or branched alkyl, or $C_{1-4}$ linear or branched alkoxy;

Y is NH or O;

$Z^1$, $Z^2$ and W are each independently $CR^7$ or N;

wherein $R^7$ is hydrogen, halogen, cyano, hydroxy, $C_{1-4}$ linear or branched alkyl, or 44 linear or branched alkoxy.

Specifically, the process of preparing the compounds of Formula (I) includes;

The step of preparing compound 3 through substitution reaction of compound 1 and compound 2 (Step 1);

The step of preparing a compound that is represented either by compound 4 or compound 6 through boronylation reaction of compound 4 and compound 6 (Step 2);

The step of preparing compound 7 through Suzuki coupling reactions of compound 3 and compound 5 or compound 4 and compound 6 (Step 3);

The step of preparing compound 9 through Mitsunobu condensation of compound 7 and compound 8 (Step 4); or The step of preparing compounds of Formula (I) through hydrolysis reaction of compound 9 (Step 5).

The preparing processes of Formula (I) can be described in more detail for each step as follows;

i) In Step 1, compound 3 can be prepared through substitution of leaving group of compound 2 with compound 1. In addition, solvents available for the reaction include N,N-dimethylformamide, acetonitrile, dimethylsulfoxide or toluene, and bases used in the reaction include cesium carbonate, potassium carbonate or sodium hydride. To be specific, the step describes preparation of compound 3 through substitution reaction of compound 1 and compound 2 with adequate solvents and bases, for example, N,N-dimethylformamide and potassium carbonate.

ii) The Step 2 describes the process of preparing compound 4 or compound 6 through boronylation reaction of compound 3 or compound 5 with equivalent or excessive use of boronylation reagents and metal catalysts. Metal catalysts, more specifically palladium catalysts, include [1,1'-Bis(diphenylphosphino)ferrocene]dichloro Palladium (II), dicholoromethane (Pd(dppf)Cl$_2$·DCM) or Palladium tetrakis(triphenylphosphine) (Pd(PPh$_3$)$_4$). In addition, solvents involved in the reaction include dichloromethane, acetonitrile, 1, 4-dioxane or toluene. The boronic-reagent can be selected from either Bis(pinacolato)diboron or Bis(neopentylglycolato)diboron. To be more specific, the process of preparing compound 4 can be described in the following reaction; A reaction of a solution of compound 3 and adequate catalysts, boronic-reagents, base and solvents, for example, 1,4-dioxane with Pd(dppf)Cl$_2$, potassium acetate and Bis(pinacolato)diboron.

iii) The Step 3 describes the process of preparing compounds that are represented by compound 7 from Suzuki coupling reaction of compound 4 or compound 6 obtained from Step 2 and compound 3 or compound 5. The coupling reaction can be processed with adequate combinations of palladium catalysts and bases, and the catalysts available for the reaction include Tetrakis(triphenylphosphine) (Pd(PPh$_3$)$_4$), Bis(triphenylphosphine)Palladium (II) dichloride (PdCl$_2$ (PPh$_3$)$_2$), Palladium dichloride (PdCl$_2$) or Palladium acetate (Pd(OCOCH$_3$)$_2$). In addition, solvents used for the reaction include tetrahydrofuran, diethylether, diphenylether, diisopropylether, N,N-dimethylformamide, dimethylacetamide, dimethylsulfoxide, dichloromethane, chlorobenzene, toluene, benzene or water or mixture of these solvents. To be more specific, the Step describes the process of preparing compound 7 through Suzuki coupling reaction of compound 3 and compound 4 with the combination of adequate solvents, catalyst, ligand and base, for example, mixture of toluene and water with Pd$_2$(dba)$_3$, biphenyl-dicyclohexylphosphine, and potassium phosphate tribasic.

iv) The Step 4 describes the process of preparing compound 9 through Mitsunobu reaction of compound 7 and compound 8. To be more specific, compound 9 can be prepared from Mitsunobu reaction of the mixture solution of compound 7 and compound 8 with triphenylphosphine and 1,1'-(azodicarbonyl)dipiperidine (ADDP) under 0.

v) The Step 5 describes the process of preparing compounds of Formula (I) through hydrolysis reaction of compound 9 under basic condition. In particular, compounds of Formula (I) can be prepared through compound 9 reacting with adequate base under room temperature, resulting the reduction of ester to carboxylic acid. Bases available for the reaction include potassium hydroxide, sodium hydroxide or lithium hydroxide. To be more specific, compounds of Formula (I) can be prepared from the reaction of compound 9 with adequate base, for example, lithium hydroxide.

The present invention provides a pharmaceutical composition for the treatment of metabolic disorders, which comprises the compounds of Formula (I), racemate, enantiomer, diastereoisomer thereof, or pharmaceutically acceptable salts thereof. Compounds of the invention intended for pharmaceutical use comprise compounds of Formula (I), their pharmaceutically acceptable salts, solution, and hydrates.

The term "prevention", as used herein, covers any inhibition or regression of diseases that are induced by the compounds of the present invention.

The term "treatment", as used herein, covers any treatment of diseases in a mammal, particularly a human, and includes inhibiting the diseases, i.e., arresting the development; or relieving the diseases, i.e. inducing regression of the diseases and/or their symptoms or conditions and slowing disease progression.

The term "metabolic disorder", as used herein, refers to any disorders caused by metabolic abnormality in lipids or glucose, and includes, but not limited to, obesity, type 2 diabetes, disturbed glucose tolerance, insulin resistance, hyperglycemia, hyperlipidemia, hypertriglyceridemia, hypercholesteremia, and dyslipidemia.

The present invention provides a method of treating metabolic disorders in a subject in need thereof, comprising administration of effective amounts of the pharmaceutical composition to the subject. The dosage of pharmaceutical composition of the present invention may vary depending on the patient's weight, age, gender, physical condition, diet, time and mode of administration, excretion rates, and severity of illness, but is readily apparent to those skilled in the art. Mammals, preferably humans, are desirable for the individuals without limit.

The term "therapeutically effective amount" refers to an amount of a compound of the present invention that ameliorates, attenuates or eliminates a particular disease or condition or prevents or delays the onset of a particular disease or condition. In the case of diabetes mellitus, the therapeutically effective amount of the drug may reduce postprandial blood glucose level; reduce HbA1c level; treat or inhibit diabetic retinopathy or nephropathy; inhibit (slow to some extent and preferably stop) progress of diabetes; weight loss; ameliorate or enhance pancreatic β-cell function; and/or relieve to some extent one or more of the symptoms associated with diabetes. To the extent the drug may modulate blood glucose level to normal state.

The "pharmaceutical composition" as used herein may contain effective component and pharmaceutically acceptable formulation, and the pharmaceutical compositions suitable for the delivery of compounds of the present invention and methods for their preparation can be readily apparent to those skilled in the art.

The pharmaceutical composition as used herein can be administered either orally or parenterally through diverse formulations, and the effective dose of administration may vary depending on physical condition, body weight and severity of the illness of the subject, formulation, and administration time and route, but can be readily determined by those skilled in the art.

Formulations suitable for oral administration include tablets, pills, solid/soft capsules, liquid, suspension, emulsifier, syrups, granules, and elixir, and typically comprise diluents (i.e. lactose, dextrose, sucrose mannitol, solbitol, cellulose, and/or glycine) and lubricant (i.e. silica, talc, stearic acid and its magnesium or calcium salt and/or polyethylene glycol). Tablets of the formulation also comprise binders including magnesium aluminium silicate, starch paste, gelatin, methyl cellulose, sodium carboxy methyl cellulose, and/or polyvenyl pyrrolidine, and depending on circumstances, tablets may comprise disintegrants including starch, agar, alginic acid or its sodium salt, or boiling mixture, absorbent, coloring agent, flavoring agents, or sweeteners.

The pharmaceutical composition as used herein is administered with pharmaceutically effective amounts. The term "pharmaceutically effective amount" refers to sufficient amount of a compound in the present invention that can treat disease with rational and adequate benefit/risk ratio, and the effective amount can be readily determined depending on the types of subject's illness, severity, activity of the compound, sensitivity of the subject to the compound, administration time, route and excretion ratio, treatment interval, factors including co-administered drugs and other well-known medical factors. Compounds of the present invention can be combined or co-administered with other types of drugs as a combination therapy or monotherapy, and can be administered with add-on therapy to the pre-existing treatment with single or multiple administration. Aforementioned factors must be all considered adequately to determine within the bounds of goal achieving maximum therapeutic effect with minimum amounts of the compound without harmful or serious adverse effects, and this process can be readily determined by those skilled in the art.

In particular, the therapeutically effective amount of the compound in the present invention can vary depending on the subject's age, gender, and body weight, and typically ranges from 0.001 to 150 mg per 1 kilogram of body weight, desirably from 0.01 to 100 mg/kg/day or 0.01 to 100 mg/kg/48 hrs with Q.D., B.I.D. or T.I.D.

The present invention explains, but not limited to, in detail through the following examples and experimental examples.

[Intermediates]

<Intermediate 1> (3S)-3-(4-Hydroxy-phenyl)-hex-4-ynoic acid methyl ester

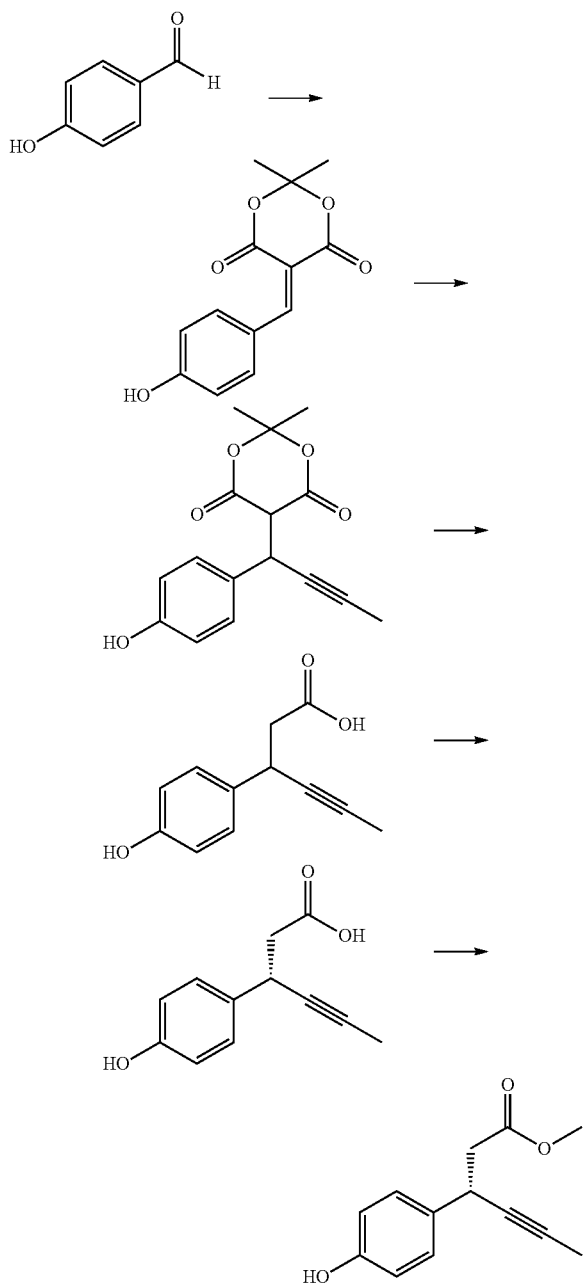

Step 1: 5-(4-Hydroxy-benzylidene)-2,2-dimethyl-[1,3]dioxane-4,6-dione

4-Hydroxybenzaldehyde (1.0 eq.) was dissolved in water (0.9 M) at 75° C.

Subsequently, a solution of meldrum's acid (1.1 eq.) in water (1.2 M) was added to the reaction mixture. The mixture was stirred at 75° C. for 2 h, and then added with a solution of meldrum's acid (0.5 eq.) in water (1.2 M). The mixture was stirred at 75° C. for another 2 h. The mixture was allowed to reach room temperature, filtered with iced-water. The wet solid was dried in an oven (50° C.) to afford 5-(4-hydroxy-benzylidene)-2,2-dimethyl-[1,3]dioxane-4,6-dione.

Step 2: (+/−)-5-[1-(4-Hydroxy-phenyl)-but-2-ynyl]-2,2-dimethyl-[1,3]dioxane-4,6-dione 1-Propynylmagnesium bromide in tetrahydrofuran (0.5 N, 3.0 eq.) was added dropwise to a solution of 5-(4-hydroxy-benzylidene)-2,2-dimethyl-1,3-dioxane-4,6-dione (1.0 eq.) in tetrahydrofuran anhydrous (0.4 M) at 4° C. under $N_2$ atmosphere. The reaction mixture was stirred at room temperature for 30 min. The mixture was quenched with saturated aqueous ammonium chloride solution and washed with hexane. After the aqueous layer was collected, the mixture was acidified with 1.0 M aqueous hydrochloric acid solution and diluted with ethyl acetate. The organic layer was washed with water and brine, dried over magnesium sulfate, filtered and concentrated. The resultant residue was purified by flash column chromatography on silica gel eluting to afford (+/−)-5-[1-(4-hydroxy-phenyl)-but-2-ynyl]-2,2-dimethyl-[1,3]dioxane-4,6-dione.

Step 3: (+/−)-3-(4-Hydroxy-phenyl)-hex-4-ynoic acid (+/−)-5-[1-(4-Hydroxy-phenyl)-but-2-ynyl]-2,2-dimethyl-[1,3]dioxane-4,6-dione (1.0 eq.) was dissolved in the mixture of 3-pentanone (0.8 M) and water (1.6 M) and stirred at 100° C. for 48 h. The mixture was allowed to reach room temperature, and basified with 3.0 M aqueous potassium hydroxide solution. The aqueous layer was collected, acidified with concentrated hydrochloric acid, and diluted with ethyl acetate. The organic layer was washed with brine, dried over magnesium sulfate, filtered and concentrated. No further purification was needed to afford (+/−)-3-(4-hydroxy-phenyl)-hex-4-ynoic acid.

Step 4: (3S)-3-(4-Hydroxy-phenyl)-hex-4-ynoic acid

A solution of (1S,2R)-1-amino-2-indanol (0.6 eq.) in acetonitrile anhydrous (0.8 M) was added to a solution of (+/−)-3-(4-hydroxy-phenyl)-hex-4-ynoic acid (1.0 eq.) in acetonitrile anhydrous (0.8 M) at 70° C. and stirred for 4 h. The mixture was allowed to reach room temperature, the salt was filtered. The salt was added in mixture of acetonitrile (0.4 M) and water (4.3 M) at 70° C. and stirred for 4 h. The reaction mixture was allowed to reach room temperature, and the salt was filtered. After two runs in the same manner, the salt was added in the mixture of ethyl acetate and water at room temperature. 2.0 M aqueous hydrochloric acid solution was added and the mixture was stirred vigorously at room temperature. After two clear layers were obtained, the layers were separated and diluted with ethyl acetate. The organic layer was washed with brine, dried over magnesium sulfate, filtered and concentrated. No further purification was needed to afford (3S)-3-(4-hydroxy-phenyl)-hex-4-ynoic acid.

Step 5: (3S)-3-(4-Hydroxy-phenyl)-hex-4-ynoic acid methyl ester

Concentrated sulfuric acid (5 drops) was added to the mixture of (3S)-3-(4-hydroxy-phenyl)-hex-4-ynoic acid (1.0 eq.) in methanol (0.5 M) at room temperature. The mixture was stirred at 90° C. for 18 h. The mixture was allowed to reach room temperature, and basified with saturated aqueous sodium bicarbonate solution and extracted with ethyl acetate. The organic layer was washed with water and brine, dried over magnesium sulfate, filtered and concentrated. No further purification was needed to afford (3S)-3-(4-hydroxyphenyl)-hex-4-ynoic acid methyl ester.

<Intermediate 2> (S)-((4-Bromo-7-fluoro-2,3-dihydro-1H-inden-1-yl)oxy)(tert-butyl)dimethylsilane

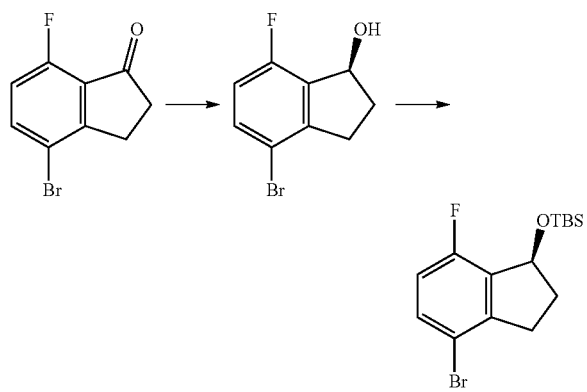

Step 1: (S)-4-Bromo-7-fluoro-2,3-dihydro-1H-inden-1-ol

Formic acid (3.5 eq.) was added to a solution of triethylamine (3.0 eq.) in dichloromethane (1.5 M) at 4° C. 4-Bromo-7-fluoro-2,3-dihydro-1H-inden-1-one (1.0 eq.) was added and then purged with $N_2$ for 5 min. Chloro{[(1S, 2S)-(−)-2-amino-1,2-diphenylethyl](4-toluenesulfonyl)amido}-(mesitylene)ruthenium(II) (0.02 eq.) was added and then stirred at room temperature for 18 h. The mixture was diluted with dichloromethane and washed with water. The organic layer was washed with brine, dried over magnesium sulfate, filtered and concentrated. The resultant residue was purified by flash column chromatography on silica gel to afford (S)-4-bromo-7-fluoro-2,3-dihydro-1H-inden-1-ol. Enantiomeric excess was confirmed by <Chiral UPCC analysis method I>.

Step 2: (S)-((4-Bromo-7-fluoro-2,3-dihydro-1H-inden-1-yl)oxy)(tert-butyl)dimethylsilane

*158
Imidazole (3.0 eq.) was added to a solution of (S)-4-bromo-7-fluoro-2,3-dihydro-1H-inden-1-ol (1.0 eq.) in dichloromethane (1.5 M) at 4° C. The reaction mixture was stirred at room temperature for 15 min. tert-Butyldimethylsillyl chloride (2.0 eq.) was added and then the mixture was allowed to reach room temperature, stirred for 1 h. The mixture was diluted with ethyl acetate and washed with water. The organic layer was washed with brine and dried over magnesium sulfate, filtered and concentrated. The resultant residue was purified by flash column chromatography on silica gel to afford (S)-((4-bromo-7-fluoro-2,3-dihydro-1H-inden-1-yl)oxy)(tert-butyl)dimethylsilane.

<Intermediate 3> (S)-4-Bromo-1-((tert-butyldimethylsilyl)oxy)-2,3-dihydro-1H-indene-5-carbonitrile

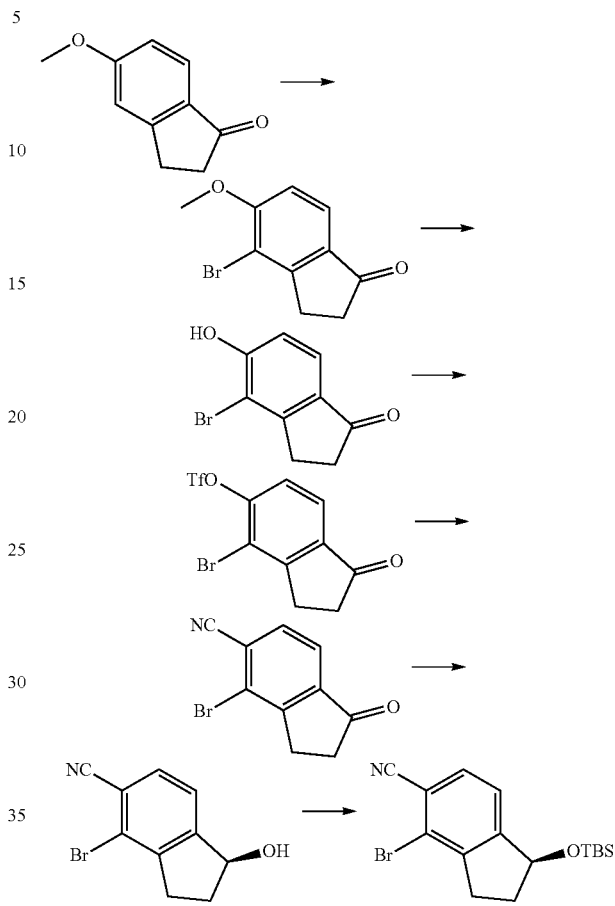

Step 1: 4-Bromo-5-methoxy-2,3-dihydro-1H-inden-1-one

N-Bromosuccinimide (1.0 eq.) was added to a solution of 5-methoxy-2,3-dihydro-1H-inden-1-one (1.0 eq.) in water (0.1 M) and the reaction mixture was heated to 60° C. 40% aqueous sulfuric acid solution (2.0 eq.) was added and stirred at 60° C. for 6 h. The crude product was extracted with tert-butyl methyl ether and dried over magnesium sulfate, filtered and concentrated. Then, the mixture was additionally purified bycrystallization using ethanol to give pure 4-bromo-5-methoxy-2,3-dihydro-1H-inden-1-one.

Step 2: 4-Bromo-5-hydroxy-2,3-dihydro-1H-inden-1-one

Sodium thiomethoxide (4.4 eq.) was added to a solution of 4-bromo-5-methoxy-2,3-dihydro-1H-inden-1-one (1.0 eq.) in N,N-dimethylformamide (1.7 M). The reaction mixture was stirred at 120° C. for 3 h. The mixture was allowed to reach room temperature, neutralized with 1.0M hydrochloride solution and diluted with ethyl acetate. The organic layer was washed with water and brine, dried over magnesium sulfate, filtered and concentrated. The resultant residue was purified by flash column chromatography on silica gel to afford 4-bromo-5-hydroxy-2,3-dihydro-1H-inden-1-one.

Step 3: 4-Bromo-1-oxo-2,3-dihydro-1H-inden-5-yl trifluoromethanesulfonate

Trifluoromethanesulfonic anhydride (1.1 eq.) was added dropwise to a solution of 2,6-lutidine (2.5 eq.) and 4-bromo-5-hydroxy-2,3-dihydro-1H-inden-1-one (1.0 eq.) in dichloromethane (3.5 M) at 4° C. The reaction mixture was allowed to reach room temperature, and stirred for 3 h. The mixture was diluted with dichloromethane and washed with saturated aqueous ammonium chloride solution. The organic layer was washed with water and brine, dried over magnesium sulfate, filtered and concentrated. The resultant residue was purified by flash column chromatography on silica gel to afford 4-bromo-1-oxo-2,3-dihydro-1H-inden-5-yl trifluoromethanesulfonate.

Step 4: 4-Bromo-1-oxo-2,3-dihydro-1H-indene-5-carbonitrile

Zinc cyanide (0.3 eq.), tris(dibbenzylideneacetone)dipalladium(0) (0.05 eq.) and 1,1-bis(diphenylphosphino)ferrocene (0.1 eq.) were added to a solution of 4-bromo-1-oxo-2,3-dihydro-1H-inden-5-yl trifluoromethanesulfonate (1.0 eq.) in N,N-dimethylformamide (0.6 M). The reaction mixture was stirred at 70° C. for 1 h. The mixture was diluted with ethyl acetate and washed with water. The organic layer was washed with brine, dried over magnesium sulfate, filtered and concentrated. The resultant residue was purified by flash column chromatography on silica gel to afford 4-bromo-1-oxo-2,3-dihydro-1H-indene-5-carbonitrile.

Step 5: (S)-4-Bromo-1-hydroxy-2,3-dihydro-1H-indene-5-carbonitrile

Formic acid (3.5 eq.) was added to a solution of triethylamine (3.0 eq.) in dichloromethane (0.2 M) at 4° C. 4-Bromo-1-oxo-2,3-dihydro-1H-indene-5-carbonitrile (1.0 eq.) was added and then purged with $N_2$ for 5 min. Chloro{[(1S,2S)-(−)-2-amino-1,2-diphenylethyl](4-toluenesulfonyl)amido}-(mesitylene)ruthenium(II) (0.02 eq.) was added and stirred at room temperature for 18 h. The mixture was diluted with dichloromethane and washed with water. The organic layer was washed with brine and dried over magnesium sulfate, filtered and concentrated. The resultant residue was purified by flash column chromatography on silica gel to afford (S)-4-bromo-1-hydroxy-2,3-dihydro-1H-indene-5-carbonitrile. Enantiomeric excess was confirmed by <Chiral UPCC analysis method I>.

Step 6: (S)-4-Bromo-1-((tert-butyldimethylsilyl)oxy)-2,3-dihydro-1H-indene-5-carbonitrile Imidazole (5.0 eq.) was added to a solution of (S)-4-bromo-1-hydroxy-2,3-dihydro-1H-indene-5-carbonitrile (1.0 eq.) in dichloromethane (0.1 M) at 4° C. The reaction mixture was stirred at room temperature for 15 min. tert-Butyldimethylsillyl chloride (5.0 eq.) was added and then the reaction mixture was allowed to reach room temperature and stirred for 1 h. The mixture was diluted with ethyl acetate and washed with water. The organic layer was washed with brine and dried over magnesium sulfate, filtered and concentrated. The resultant residue was purified by flash column chromatography on silica gel to afford (S)-4-bromo-1-((tert-butyldimethylsilyl) oxy)-2,3-dihydro-1H-indene-5-carbonitrile.

<Intermediate 4> (S)-((4-Bromo-5-fluoro-2,3-dihydro-1H-inden-1-yl)oxy)(tert-butyl)dimethylsilane

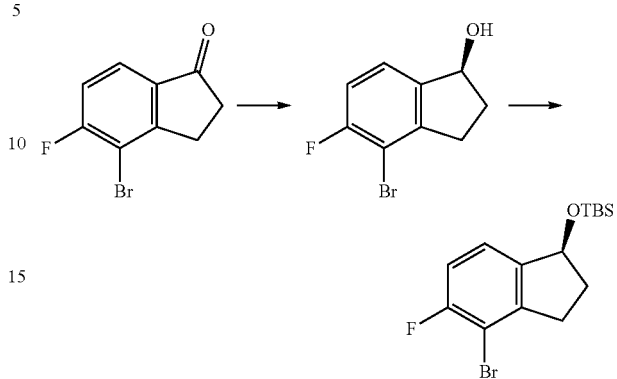

Step 1: (S)-4-Bromo-5-fluoro-2,3-dihydro-1H-inden-1-ol

Formic acid (3.5 eq.) was added to a solution of triethylamine (3.0 eq.) in dichloromethane (0.2 M) at 4° C. 4-Bromo-5-fluoro-2,3-dihydro-1H-inden-1-one (1.0 eq.) was added and then purged with $N_2$ for 5 min. Chloro{[(1S,2S)-(−)-2-amino-1,2-diphenylethyl](4-toluenesulfonyl)amido}-(mesitylene)ruthenium(II) (0.02 eq.) was added and stirred at room temperature for 18 h. The mixture was diluted with dichloromethane and washed with water. The organic layer was washed with brine and dried over magnesium sulfate, filtered and concentrated. The resultant residue was purified by flash column chromatography on silica gel to afford (S)-4-bromo-5-fluoro-2,3-dihydro-1H-inden-1-ol. Enantiomeric excess was confirmed by <Chiral UPCC analysis method I>.

Step 2: (S)-((4-Bromo-5-fluoro-2,3-dihydro-1H-inden-1-yl)oxy)(tert-butyl)dimethylsilane

*194

Imidazole (3.0 eq.) was added to a solution of (S)-4-bromo-5-fluoro-2,3-dihydro-1H-inden-1-ol (1.0 eq.) in dichloromethane (1.5 M) at 4° C. The reaction mixture was stirred at room temperature for 15 min. tert-Butyldimethylsillyl chloride (2.0 eq.) was added and then the reaction mixture was allowed to reach room temperature, stirred for 18 h. The mixture was diluted with ethyl acetate and washed with water. The organic layer was washed with brine and dried over magnesium sulfate, filtered and concentrated. The resultant residue was purified by flash column chromatography on silica gel to afford (S)-((4-bromo-5-fluoro-2,3-dihydro-1H-inden-1-yl)oxy)(tert-butyl)dimethylsilane.

<Intermediate 5> (S)-((4-Bromo-5-methoxy-2,3-dihydro-1H-inden-1-yl)oxy)(tert-butyl)dimethylsilane

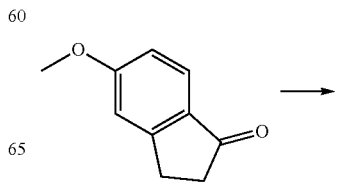

19

-continued

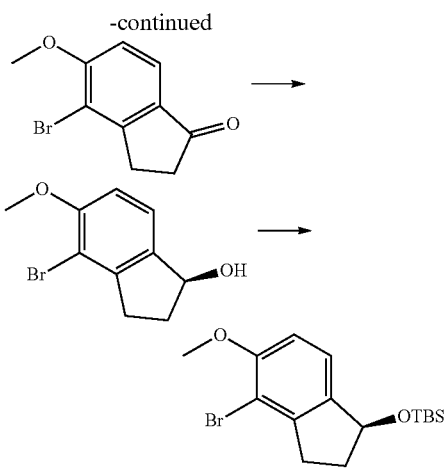

Step 1:
4-Bromo-5-methoxy-2,3-dihydro-1H-inden-1-one

N-Bromosuccinimide (1.0 eq.) was added to a solution of 5-methoxy-2,3-dihydro-1H-inden-1-one (1.0 eq.) in water (0.1 M) and the reaction mixture was heated to 60° C. 40% aqueous sulfuric acid solution (2.0 eq.) was added and stirred for 6 h. The crude product was extracted with tert-butyl methyl ether and dried over magnesium sulfate, filtered and concentrated. Then the mixture was additionally purified by crystallization using ethanol to afford pure 4-bromo-5-methoxy-2,3-dihydro-1H-inden-1-one.

Step 2: (S)-4-Bromo-5-methoxy-2,3-dihydro-1H-inden-1-ol

Formic acid (3.5 eq.) was added to a solution of triethylamine (3.0 eq.) in dichloromethane (0.2 M) at 4° C. 4-Bromo-5-methoxy-2,3-dihydro-1H-inden-1-one (1.0 eq.) was added and then the mixture was purged with N$_2$ for 5 min. Chloro{[(1S)-(−)-2-amino-1,2-diphenylethyl](4-toluenesulfonyl)amido}-(mesitylene)ruthenium(II) (0.02 eq.) was added and stirred at room temperature for 18 h. The mixture was diluted with dichloromethane and washed with water. The organic layer was washed with brine and dried over magnesium sulfate, filtered and concentrated. The resultant residue was purified by flash column chromatography on silica gel to afford (S)-4-bromo-5-methoxy-2,3-dihydro-1H-inden-1-ol. Enantiomeric excess was confirmed by <Chiral UPCC analysis method I>.

Step 3: (S)-((4-Bromo-5-methoxy-2,3-dihydro-1H-inden-1-yl)oxy)(tert-butyl)dimethylsilane Imidazole (5.0 eq.) was added to a solution of (S)-4-bromo-5-methoxy-2,3-dihydro-1H-inden-1-ol (1.0 eq.) in dichloromethane (0.1 M) at 4° C. The reaction mixture was stirred at room temperature for 15 min. tert-Butyldimethylsillyl chloride (5.0 eq.) was added and then the reaction mixture was allowed to reach room temperature, stirred for 1 h. The mixture was diluted with ethyl acetate and washed with water. The organic layer was washed with brine and dried over magnesium sulfate, filtered and concentrated. The resultant residue was purified by flash column chromatography on silica gel to afford (S)-((4-bromo-5-methoxy-2,3-dihydro-1H-inden-1-yl)oxy)(tert-butyl)dimethylsilane.

20

<Intermediate 6> (S)-5-(1-((tert-Butyldimethylsilyl)oxy)-5-methoxy-2,3-dihydro-1H-inden-4-yl)-2-((tetrahydro-2H-pyran-4-yl)oxy)pyridine

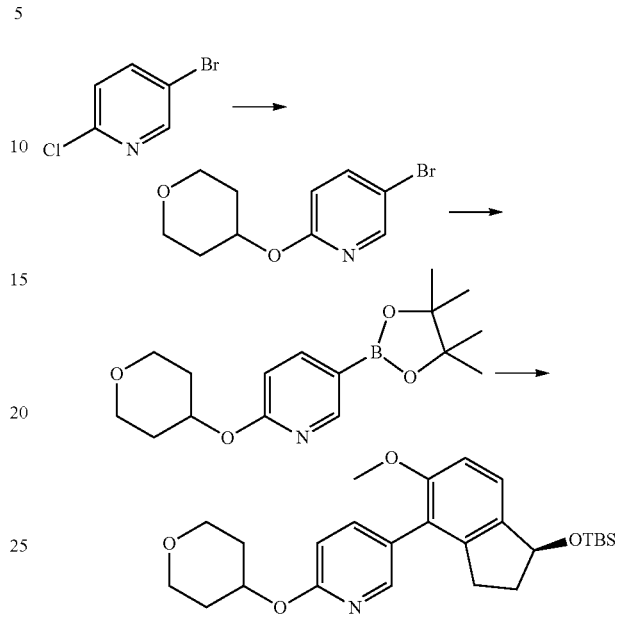

Step 1: 5-Bromo-2-((tetrahydro-2H-pyran-4-yl)oxy)pyridine

Sodium hydride (1.3 eq.) was slowly added to a solution of tetrahydro-2H-pyran-4-ol (1.0 eq.) and 5-bromo-2-chloropyridine (1.2 eq.) in N,N-dimethylformamide (0.8 M) and the reaction mixture was stirred at 60° C. for 18 h. The reaction mixture was allowed to reach room temperature, quenched with water. The mixture was diluted with ethyl acetate and washed with water. The organic layer was washed with brine and dried over magnesium sulfate, filtered and concentrated. The resultant residue was purified by flash column chromatography on silica gel to afford 5-bromo-2-((tetrahydro-2H-pyran-4-yl)oxy)pyridine.

Step 2: 2-((Tetrahydro-2H-pyran-4-yl)oxy)-5-(4,4,5,5-tetramethyl-1,3,2-dioxaborolan-2-yl)pyridine Potassium acetate (2.0 eq.) was added to a solution of 5-bromo-2-((tetrahydro-2H-pyran-4-yl) oxy) pyridine (1.0 eq.) and bis(pinacolato)diboron (1.2 eq.) in 1,4-dioxane (0.1 M) and then purged with N$_2$ for 10 min. The reaction mixture was stirred at 110° C. for 18 h. The reaction mixture was allowed to reach room temperature, diluted with ethyl acetate and washed with water. The organic layer was washed with brine and dried over magnesium sulfate, filtered and concentrated. The resultant residue was purified by flash column chromatography on silica gel to afford 2-((tetrahydro-2H-pyran-4-yl)oxy)-5-(4,4,5,5-tetramethyl-1,3,2-dioxaborolan-2-yl)pyridine.

Step 3: (S)-5-(1-((tert-Butyldimethylsilyl)oxy)-5-methoxy-2,3-dihydro-1H-inden-4-yl)-2-((tetrahydro-2H-pyran-4-yl)oxy)pyridine Tris(dibenzylideneacetone)dipalladium(0) (0.05 eq.) was added to a solution of (S)-((4-bromo-5-methoxy-2,3-dihydro-1H-inden-1-yl)oxy)(tert-butyl)dimethylsilane (1.0 eq.), 2-((tetrahydro-2H-pyran-4-yl)oxy)-5-(4,4,5,5-tetramethyl-1,3,2-dioxaborolan-2-yl)pyridine (1.2 eq.), 2-dicyclohexylphosphino-2',6'-dimethoxybiphenyl (0.1 eq.), and potassium phosphate tribasic (3.0 eq.) in toluene (0.1 M) and water (1.0 M) and then purged with N₂ for 10 min. The reaction mixture was stirred at 120° C. for 18 h under N₂ atmosphere. The reaction mixture was allowed to reach room temperature, filtered through Celite. The filtrate was diluted with ethyl acetate and washed with water. The organic layer was washed with brine and dried over magnesium sulfate, filtered and concentrated. The resultant residue was purified by flash column chromatography on silica gel to afford (S)-5-(1-((tert-butyldimethylsilyl)oxy)-5-methoxy-2,3-dihydro-1H-inden-4-yl)-2-((tetrahydro-2H-pyran-4-yl)oxy)pyridine.

<Intermediate 7>
3-(6-Hydroxypyridin-3-yl)hex-4-ynoic acid ethyl ester

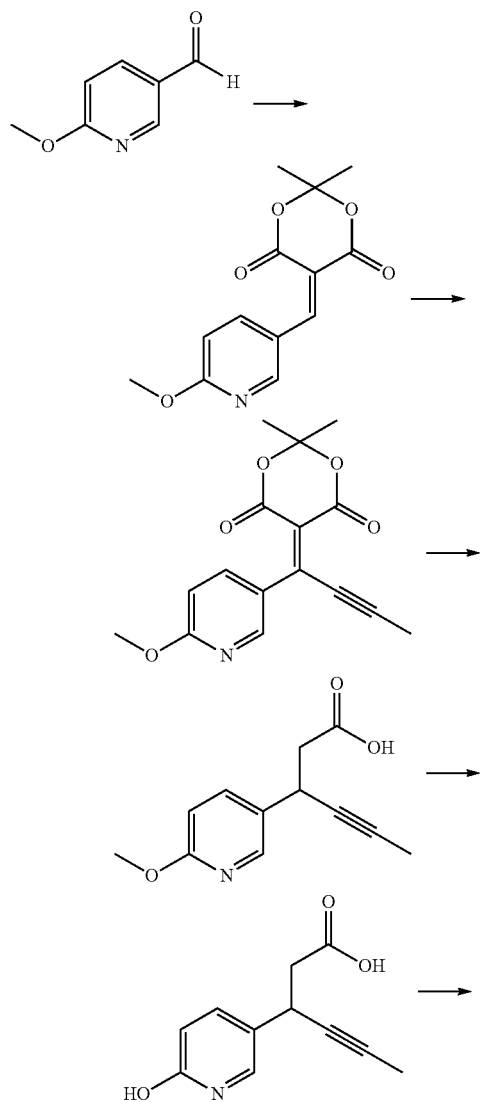

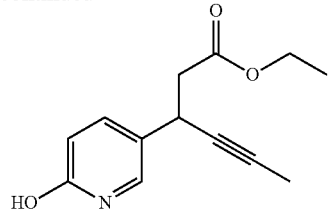

Step 1: 5-((6-Methoxypyridin-3-yl)methylene)-2,2-dimethyl-1,3-dioxane-4,6-dione

6-Methoxypyridine-3-carbaldehyde (1.0 eq.) was dissolved in water (0.9 M) at 75° C. Subsequently, a solution of meldrum's acid (1.1 eq.) in water (1.2 M) was added to the mixture. The mixture was stirred at 75° C. for 2 h, and then added with a solution of meldrum's acid (0.5 eq.) in water (1.2 M). The reaction mixture was stirred at 75° C. for 2 h. The mixture was allowed to reach room temperature, filtered with iced-water. The wet solid resultant was dried in an oven (50° C.) to afford 5-((6-methoxypyridin-3-yl) methylene)-2,2-dimethyl-1, 3-dioxane-4,6-dione.

Step 2: 5-(1-(6-Methoxypyridin-3-yl)but-2-ynyl)-2,2-dimethyl-1,3-dioxane-4,6-dione A solution of 5-((6-methoxypyridin-3-yl)methylene)-2,2-dimethyl-1,3-dioxane-4,6-dione (1.0 eq.) in tetrahydrofuran anhydrous (0.4 M) was added dropwise to 1-propynylmagnesium bromide in tetrahydrofuran (0.5 N, 1.5 eq.) at 4° C. under N₂ atmosphere. The mixture was stirred at room temperature for 30 min. The mixture was quenched with saturated aqueous ammonium chloride solution and extracted with hexane. After the aqueous layer was collected, the mixture was acidified with 1.0 M aqueous hydrochloric acid solution and diluted with ethyl acetate. The organic layer was washed with water and brine, dried over magnesium sulfate, filtered and concentrated. The resultant residue was purified by flash column chromatography on silica gel eluting to afford 5-(1-(6-methoxypyridin-3-yl)but-2-ynyl)-2,2-dimethyl-1,3-dioxane-4,6-dione.

Step 3: 3-(6-Methoxypyridin-3-yl)hex-4-ynoic acid 5-(1-(6-Methoxypyridin-3-yl)but-2-ynyl)-2,2-dimethyl-1,3-dioxane-4,6-dione (1.0 eq.) was dissolved in the mixture of N,N-dimethylformamide (0.2 M) and water (2.0 M) at 100° C. and stirred for 18 h. The reaction mixture was allowed to reach room temperature, quenched with saturated aqueous ammonium chloride solution and the extracted with ethyl acetate. The organic layer was washed with brine, dried over magnesium sulfate, filtered and concentrated. No further purification was needed to afford 3-(6-methoxypyridin-3-yl)hex-4-ynoic acid.

Step 4: 3-(6-Hydroxypyridin-3-yl) hex-4-ynoic acid

Concentrated hydrochloric acid solution (8.0 M) was added to the mixture of 3-(6-methoxypyridin-3-yl)hex-4-ynoic acid (1.0 eq.) in 1,4-dioxane (2.0 M) and water (2.0 M) at room temperature. The mixture was stirred at 100° C. for 18 h under N₂ atmosphere. The reaction mixture was allowed to reach room temperature, basified with saturated aqueous sodium bicarbonate solution and extracted with ethyl acetate. The organic layer was washed with brine, dried over magnesium sulfate, filtered and concentrated. No further purification was needed to afford 3-(6-hydroxypyridin-3-yl) hex-4-ynoic acid.

Step 5: 3-(6-Hydroxypyridin-3-yl) hex-4-ynoic acid ethyl ester

Concentrated sulfuric acid (5 drops) was added to the mixture of 3-(6-hydroxypyridin-3-yl) hex-4-ynoic acid (1.0 eq.) in ethanol (0.9 M) at room temperature. The mixture was stirred at 90° C. for 18 h. The reaction mixture was allowed to reach room temperature, basified with saturated aqueous sodium bicarbonate solution and extracted with ethyl acetate. The organic layer was washed with water and brine, dried over magnesium sulfate, filtered and concentrated. No further purification was needed to afford 3-(6-hydroxypyridin-3-yl) hex-4-ynoic acid ethyl ester.

<Intermediate 8> (S)-3-(4-(((R)-4-(5-Chloro-6-((tetrahydro-2H-pyran-4-yl)oxy)pyridin-3-yl)-7-fluoro-2,3-dihydro-1H-inden-1-yl)oxy)phenyl)hex-4-ynoate methyl ester

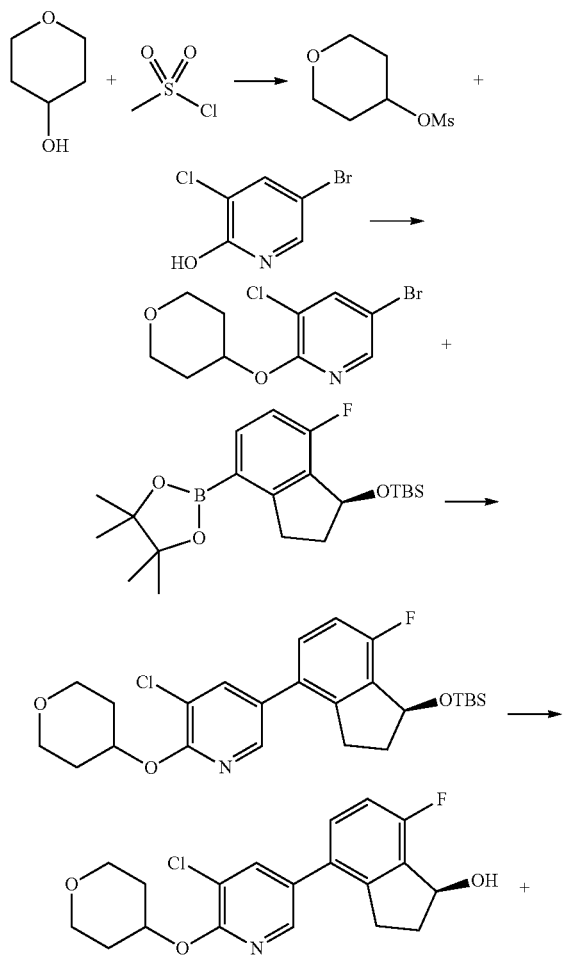

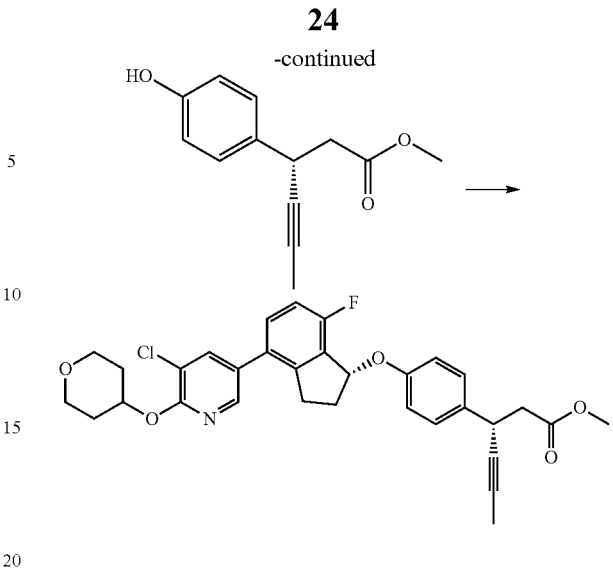

Step 1: Tetrahydro-2H-pyran-4-yl methanesulfonate

Methanesulfonyl chloride (1.2 eq.) was added to a solution of tetrahydro-2H-pyran-4-ol (1.0 eq.) and triethylamine (3.0 eq.) in dichloromethane (0.3 M) at 4° C. The reaction mixture was stirred at room temperature for 1 h. The mixture was diluted with dichloromethane and washed with water. The organic layer was washed with brine, saturated aqueous ammonium chloride, and dried over magnesium sulfate, filtered and concentrated. The resultant residue was purified by flash column chromatography on silica gel to afford tetrahydro-2H-pyran-4-yl methanesulfonate.

Step 2: 5-Bromo-3-chloro-2-((tetrahydro-2H-pyran-4-yl)oxy)pyridine

Potassium carbonate (2.0 eq.) was added to a solution of tetrahydro-2H-pyran-4-yl methanesulfonate (1.2 eq.) and 5-bromo-3-chloropyridine-1-ol (1.0 eq.) in N,N-dimethylformamide (0.2 M). The reaction mixture was stirred at 100° C. for 18 h. The reaction mixture was allowed to reach room temperature, diluted with ethyl acetate and washed with water. The organic layer was washed with brine, dried over magnesium sulfate, filtered and concentrated. The resultant residue was purified by flash column chromatography on silica gel to afford 5-bromo-3-chloro-2-((tetrahydro-2H-pyran-4-yl) oxy) pyridine.

Step 3: (S)-5-(1-((tert-Butyldimethylsilyl)oxy)-7-fluoro-2,3-dihydro-1H-inden-4-yl)-3-chloro-2-((tetrahydro-2H-pyran-4-yl)oxy)pyridine Tris(dibenzylideneacetone)dipalladium(0) (0.05 eq.) was added to a solution of 5-bromo-3-chloro-2-((tetrahydro-2H-pyran-4-yl)oxy)pyridine (1.0 eq.), (S)-tert-butyl((7-fluoro-4-(4,4,5,5-tetramethyl-1,3,2-dioxaborolan-2-yl)-2,3-dihydro-1H-inden-1-yl)oxy)dimethylsilane (1.2 eq.), 2-dicyclohexylphosphino-2',6'-dimethoxybiphenyl (0.1 eq.), and potassium phosphate tribasic (3.0 eq.) in toluene (0.1 M) and water (1.0 M) and then purged with $N_2$ atmosphere for 10 min. The reaction mixture was stirred at 120° C. for 18 h under $N_2$ atmosphere. The reaction mixture was allowed to reach room temperature, filtered through Celite. The filtrate was diluted with ethyl acetate and washed with water. The organic layer was washed with brine, dried over magnesium sulfate, filtered and concentrated. The resultant residue was purified by flash column chromatography on silica gel to afford (S)-5-(1-((tert-butyldimethylsilyl)oxy)-7-fluoro-2,3-dihydro-1H-inden-4-yl)-3-chloro-2-((tetrahydro-2H-pyran-4-yl)oxy)pyridine.

Step 4: (S)-4-(5-Chloro-6-((tetrahydro-2H-pyran-4-yl)oxy)pyridin-3-yl)-7-fluoro-2,3-dihydro-1H-inden-1-ol 1.0 M Tetra-n-butyl ammonium fluoride (2.0 eq.) was added dropwise to a solution of (S)-5-(1-((tert-butyldimethylsilyl)oxy)-7-fluoro-2,3-dihydro-1H-inden-4-yl)-3-chloro-2-((tetrahydro-2H-pyran-4-yl)oxy)pyridine (1.0 eq.) in tetrahydrofuran (0.1 M) at 4° C. The reaction mixture was stirred at room temperature for 4 h. The mixture was diluted with ethyl acetate and washed with water. The organic layer was washed with brine and dried over magnesium sulfate, filtered and concentrated. The resultant residue was purified by flash column chromatography on silica gel to afford (S)-4-(5-chloro-6-((tetrahydro-2H-pyran-4-yl)oxy)pyridin-3-yl)-7-fluoro-2,3-dihydro-1H-inden-1-ol.

Step 5: (S)-3-(4-(((R)-4-(5-Chloro-6-((tetrahydro-2H-pyran-4-yl)oxy)pyridin-3-yl)-7-fluoro-2, 3-dihydro-1H-inden-1-yl)oxy)phenyl)hex-4-ynoate methyl ester 1,1'-(Azodicarbonyl)dipiperidine (1.5 eq.) was added portionwise over 10 min to a solution of (S)-4-(5-chloro-6-((tetrahydro-2H-pyran-4-yl)oxy)pyridin-3-yl)-7-fluoro-2,3-dihydro-1H-inden-1-ol (1.0 eq.), (3S)-3-(4-hydroxyphenyl)-hex-4-ynoic acid methyl ester (1.0 eq.), and tri-n-butylphosphine (1.5 eq.) in toluene (0.1 M) at 4° C. The mixture was stirred at room temperature for 18 h. After addition of hexane (0.05 M) to reaction mixture, the resulting white solid was removed by filtration. The filtrate was concentrated and then purified by flash column chromatography on silica gel to afford (S)-3-(4-(((R)-4-(5-chloro-6-((tetrahydro-2H-pyran-4-yl)oxy)pyridin-3-yl)-7-fluoro-2,3-dihydro-1H-inden-1-yl)oxy)phenyl)hex-4-ynoate methyl ester.

<Intermediate 9> Chiral UPCC Analysis Method I

Flow rate: 2 mL/min.
Mobile phase: Isocratic CO$_2$/Ethanol (80/20)
Stationary phase: CHIRALPAK-IA 250*4.6 mm I.D.
Temperature: 25° C.
Absorbance Wavelength: 220 nm

EXAMPLES

Example 1

(S)-3-(4-(((R)-4-(6-((1,1-Dioxidotetrahydro-2H-thiopyran-4-yl)oxy)pyridin-3-yl)-7-fluoro-2,3-dihydro-1H-inden-1-yl)oxy)phenyl)hex-4-ynoic acid

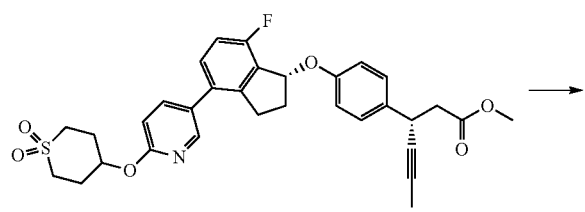

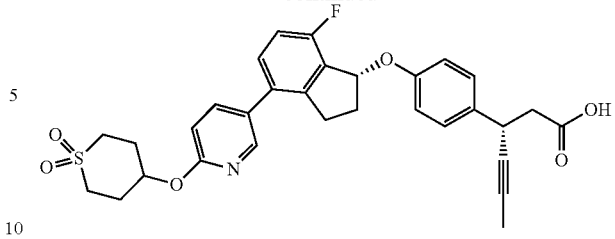

2.0 M aqueous lithium hydroxide solution (5.0 eq.) was added to a solution of (S)-3-(4-(((R)-4-(6-((1,1-dioxidotetrahydro-2H-thiopyran-4-yl)oxy)pyridin-3-yl)-7-fluoro-2,3-dihydro-1H-inden-1-yl)oxy)phenyl)hex-4-ynoic acid methyl ester (1.0 eq.) in tetrahydrofuran (1.0 M) and methanol (4.0 M) at 4° C. The mixture was stirred at room temperature for 18 h. The mixture was neutralized with saturated aqueous ammonium chloride solution and diluted with ethyl acetate. The organic layer was washed with brine, dried over magnesium sulfate, filtered, and concentrated. The resultant residue was purified by flash column chromatography on silica gel to afford (S)-3-(4-(((R)-4-(6-((1,1-dioxidotetrahydro-2H-thiopyran-4-yl)oxy)pyridin-3-yl)-7-fluoro-2,3-dihydro-1H-inden-1-yl)oxy)phenyl)hex-4-ynoic acid. MS ESI (positive) m/z: 564.15 (M+H).
$^1$H NMR (400 MHz, CDCl$_3$) δ 8.18 (s, 1H), 7.69 (d, J=8.4 Hz, 1H), 7.34 (d, J=8.4 Hz, 2H), 7.29-7.25 (m, 1H), 7.04 (t, J=8.4 Hz, 1H), 6.96 (d, J=8.4 Hz, 2H), 6.83 (d, J=8.4 Hz, 1H), 5.93 (s, 1H), 5.45 (s, 1H), 4.16-4.07 (m, 1H), 3.44-3.37 (m, 2H), 3.32-3.23 (m, 1H), 3.03-2.98 (m, 2H), 2.90-2.80 (m, 2H), 2.76-2.71 (m, 1H), 2.57-2.54 (m, 2H), 2.48-2.32 (m, 4H), 1.84 (d, J=2.4 Hz, 3H).

Example 2

(S)-3-(4-(((R)-7-Fluoro-4-(6-((3-methyloxetan-3-yl)methoxy)pyridin-3-yl)-2,3-dihydro-1H-inden-1-yl)oxy)phenyl)hex-4-ynoic acid The title compound was synthesized from (S)-3-(4-(((R)-7-fluoro-4-(6-((3-methyloxetan-3-yl)methoxy)pyridin-3-yl)-2,3-dihydro-1H-inden-1-yl)oxy)phenyl)hex-4-ynoic acid methyl ester through the same procedure as used in Example 1. MS ESI (positive) m/z: 516.15 (M+H).
$^1$H NMR (400 MHz, CDCl$_3$) δ 8.21 (d, J=2.4 Hz, 1H), 7.67-7.65 (m, 1H), 7.33-7.28 (m, 3H), 7.03 (t, J=8.6 Hz, 1H), 6.97-6.95 (m, 2H), 6.86 (d, J=8.4 Hz, 1H), 5.93-5.91 (m, 1H), 4.68 (d, J=5.6 Hz, 2H), 4.47 (d, J=5.6 Hz, 2H), 4.42 (s, 2H), 4.09-4.08 (m, 1H), 3.28-3.26 (m, 1H), 2.92-2.85 (m, 1H), 2.81-2.65 (m, 2H), 2.39-2.36 (m, 2H), 1.84 (d, J=2.4 Hz, 3H).

Example 3

(S)-3-(4-(((R)-4-(6-(2-(1,1-Dioxidothiomorpholino)ethoxy)pyridin-3-yl)-7-fluoro-2,3-dihydro-1H-inden-1-yl)oxy)phenyl)hex-4-ynoic acid The title compound was synthesized from (S)-3-(4-(((R)-4-(6-(2-(1,1-dioxidothiomorpholino)ethoxy)pyridin-3-yl)-7-fluoro-2,3-dihydro-1H-inden-1-yl)oxy)phenyl)hex-4-ynoic acid methyl ester through the same procedure as used in Example 1. MS ESI (positive) m/z: 593.08 (M+H).
$^1$H NMR (400 MHz, CDCl$_3$) δ 8.16 (d, J=2.4 Hz, 1H), 7.65 (dd, J=8.6, 2.4 Hz, 1H), 7.35-7.26 (m, 3H), 7.08-7.00 (m, 1H), 6.95 (d, J=8.4 Hz, 2H), 6.81 (d, J=8.8 Hz, 1H), 5.92

(t, J=2.6 Hz, 1H), 4.49 (t, J=5.4 Hz, 2H), 4.11-4.02 (m, 1H), 3.29-3.15 (m, 5H), 3.15-2.99 (m, 6H), 2.90-2.70 (m, 3H), 2.42-2.35 (m, 2H), 1.84 (d, J=2.4 Hz, 3H).

Example 4

(S)-3-(4-(((R)-7-Fluoro-4-(6-(oxetan-3-yloxy)pyridin-3-yl)-2,3-dihydro-1H-inden-1-yl)oxy)phenyl)hex-4-ynoic acid The title compound was synthesized from (S)-3-(4-(((R)-7-fluoro-4-(6-(oxetan-3-yloxy)pyridin-3-yl)-2,3-dihydro-1H-inden-1-yl)oxy)phenyl)hex-4-ynoic acid methyl ester through the same procedure as used in Example 1. MS ESI (positive) m/z: 488.12 (M+H).
$^1$H NMR (400 MHz, CDCl$_3$) δ 8.12 (s, 1H), 7.67 (d, J=4.4 Hz, 1H), 7.33-7.24 (m, 3H), 7.01 (t, J=2.4 Hz, 1H), 6.98 (d, J=8.4 Hz, 2H), 6.86 (d, J=4.8 Hz, 1H), 5.92 (t, J=2.6 Hz, 1H), 5.67 (t, J=5.4 Hz, 1H), 5.04-5.01 (m, 2H), 4.79-4.76 (m, 2H), 4.09-4.06 (m, 1H), 3.29-3.25 (m, 1H), 2.81-2.79 (m, 1H), 2.78-2.75 (m, 1H), 2.74-2.70 (m, 1H), 2.39-2.35 (m, 2H), 1.84 (s, 3H).

Example 5

(S)-3-(4-(((R)-7-Fluoro-4-(6-(((R)-tetrahydrofuran-3-yl)oxy)pyridin-3-yl)-2,3-dihydro-1H-inden-1-yl)oxy)phenyl)hex-4-ynoic acid The title compound was synthesized from (S)-3-(4-(((R)-7-fluoro-4-(6-(((R)-tetrahydrofuran-3-yl)oxy)pyridin-3-yl)-2,3-dihydro-1H-inden-1-yl)oxy)phenyl)hex-4-ynoic acid methyl ester through the same procedure as used in Example 1. MS ESI (positive) m/z: 502.24 (M+H).
$^1$H NMR (400 MHz, CDCl$_3$) δ 8.15 (d, J=2.4 Hz, 1H), 7.64 (dd, J=8.6, 2.6 Hz, 1H), 7.38-7.26 (m, 3H), 7.03 (t, J=8.6 Hz, 1H), 6.98-6.93 (m, 2H), 6.81 (dd, J=8.4, 0.4 Hz, 1H), 5.95-5.91 (m, 1H), 5.61-5.58 (m, 1H), 4.11-3.89 (m, 5H), 3.29-3.19 (m, 1H), 2.91-2.71 (m, 3H), 2.42-2.15 (m, 4H), 1.84 (d, J=2.4 Hz, 3H).

Example 6

(S)-3-(4-(((R)-7-Fluoro-4-(6-((tetrahydro-2H-pyran-4-yl)oxy)pyridin-3-yl)-2,3-dihydro-1H-inden-1-yl)oxy)phenyl)hex-4-ynoic acid The title compound was synthesized from (S)-3-(4-(((R)-7-fluoro-4-(6-((tetrahydro-2H-pyran-4-yl)oxy)pyridin-3-yl)-2,3-dihydro-1H-inden-1-yl)oxy)phenyl)hex-4-ynoic acid methyl ester through the same procedure as used in Example 1. MS ESI (positive) m/z: 516.06 (M+H).
$^1$H NMR (400 MHz, CDCl$_3$) δ 8.15 (d, J=2.4 Hz, 1H), 7.63 (dd, J=8.6, 2.6 Hz, 1H), 7.33 (d, J=8.4 Hz, 2H), 7.29-7.26 (m, 1H), 7.02 (t, J=8.6 Hz, 1H), 6.95 (d, J=8.4 Hz, 2H), 6.79 (d, J=8.4 Hz, 1H), 5.92-5.90 (m, 1H), 5.26-5.25 (m, 1H), 4.07-4.02 (m, 1H), 4.00-3.98 (m, 2H), 3.65-3.60 (m, 2H), 3.25-3.21 (m, 1H), 2.86-2.80 (m, 2H), 2.75-2.70 (m, 1H), 2.37-2.34 (m, 2H), 2.11-2.07 (m, 2H), 1.85-1.80 (m, 5H).

Example 7

(S)-3-(4-(((R)-7-Fluoro-4-(6-MS)-tetrahydrofuran-3-yl)oxy)pyridin-3-yl)-2,3-dihydro-1H-inden-1-yl)oxy)phenyl)hex-4-ynoic acid The title compound was synthesized from (S)-3-(4-(((R)-7-fluoro-4-(6-(((S)-tetrahydrofuran-3-yl)oxy)pyridin-3-yl)-2,3-dihydro-1H-inden-1-yl)oxy)phenyl)hex-4-ynoic acid methyl ester through the same procedure as used in Example 1. MS ESI (positive) m/z: 502.15 (M+H).
$^1$H NMR (400 MHz, CDCl$_3$) δ 8.15 (d, J=2.4 Hz, 1H), 7.64 (dd, J=8.6, 2.6 Hz, 1H), 7.38-7.26 (m, 3H), 7.03 (t, J=8.6 Hz, 1H), 6.98-6.93 (m, 2H), 6.81 (dd, J=8.4, 0.4 Hz, 1H), 5.95-5.91 (m, 1H), 5.61-5.58 (m, 1H), 4.11-3.89 (m, 5H), 3.29-3.19 (m, 1H), 2.91-2.71 (m, 3H), 2.42-2.15 (m, 4H), 1.84 (d, J=2.4 Hz, 3H).

Example 8

(S)-3-(4-(((R)-7-Fluoro-4-(4-methyl-6-(((R)-tetrahydrofuran-3-yl)oxy)pyridin-3-yl)-2,3-dihydro-1H-inden-1-yl)oxy)phenyl)hex-4-ynoic acid The title compound was synthesized from (S)-3-(4-(((R)-7-fluoro-4-(4-methyl-6-(((R)-tetrahydrofuran-3-yl)oxy)pyridin-3-yl)-2,3-dihydro-1H-inden-1-yl)oxy)phenyl)hex-4-ynoic acid methyl ester through the same procedure as used in Example 1. MS ESI (positive) m/z: 516.19 (M+H).
$^1$H NMR (400 MHz, CDCl$_3$) δ 7.78 (s, 1H), 7.31 (d, J=8.4 Hz, 2H), 7.16-7.12 (m, 1H), 7.01 (t, J=8.4 Hz, 1H), 6.91 (d, J=8.4 Hz, 2H), 6.67 (s, 1H), 5.95 (d, J=5.6 Hz, 1H), 5.58-5.52 (m, 1H), 4.10-3.84 (m, 5H), 2.88-2.71 (m, 3H), 2.65-2.47 (m, 1H), 2.44-2.22 (m, 3H), 2.20-2.11 (m, 1H), 2.11 (s, 3H), 1.84 (d, J=2.4 Hz, 3H).

Example 9

(S)-3-(4-(((R)-7-Fluoro-4-(2-methyl-6-((((R)-tetrahydrofuran-3-yl)oxy)pyridin-3-yl)-2,3-dihydro-1H-inden-1-yl)oxy)phenyl)hex-4-ynoic acid The title compound was synthesized from (S)-3-(4-(((R)-7-fluoro-4-(2-methyl-6-(((R)-tetrahydrofuran-3-yl)oxy)pyridin-3-yl)-2,3-dihydro-1H-inden-1-yl)oxy)phenyl)hex-4-ynoic acid methyl ester through the same procedure as used in Example 1. MS ESI (positive) m/z: 516.11 (M+H).
$^1$H NMR (400 MHz, CDCl$_3$) δ 7.38-7.31 (m, 3H), 7.16-7.10 (m, 1H), 7.02-6.95 (m, 3H), 6.60 (d, J=8.4 Hz, 1H), 5.94 (d, J=4.8 Hz, 1H), 5.63-5.58 (m, 1H), 4.16-3.87 (m, 5H), 3.02-2.92 (m, 1H), 2.88-2.69 (m, 2H), 2.65-2.55 (m, 1H), 2.48-2.37 (m, 1H), 2.35-2.13 (m, 6H), 1.84 (d, J=2.4 Hz, 3H).

Example 10

(S)-3-(4-(((R)-4-(5-Chloro-6-(((R)-tetrahydrofuran-3-yl)oxy)pyridin-3-yl)-7-fluoro-2,3-dihydro-1H-inden-1-yl)oxy)phenyl)hex-4-ynoic acid The title compound was synthesized from (S)-3-(4-(((R)-4-(5-chloro-6-(((R)-tetrahydrofuran-3-yl)oxy)pyridin-3-yl)-7-fluoro-2,3-dihydro-1H-inden-1-yl)oxy)phenyl)hex-4-ynoic acid methyl ester through the same procedure as used in Example 1. MS ESI (positive) m/z: 536.15 (M+H).
$^1$H NMR (400 MHz, CDCl$_3$) δ 7.97 (s, 1H), 7.61 (s, 1H), 7.25 (d, J=8.4 Hz, 2H), 7.21 (t, J=8.4 Hz, 1H), 6.93 (t, J=8.4 Hz, 1H), 6.83 (t, J=8.4 Hz, 2H), 5.79 (t, J=4.6 Hz, 1H), 5.54-5.52 (m, 1H), 4.04-3.97 (m, 5H), 3.21-3.16 (m, 1H), 2.88-2.67 (m, 3H), 2.28-2.17 (m, 4H), 1.74 (s, 3H).

319 Example 11

(S)-3-(4-(((R)-7-Fluoro-4-(5-(((R)-tetrahydrofuran-3-yl)oxy)pyridin-2-yl)-2,3-dihydro-1H-inden-1-yl)oxy)phenyl)hex-4-ynoic acid The title compound was synthesized from (S)-3-(4-(((R)-7-fluoro-4-(5-(((R)-tetrahydrofuran-3-yl)oxy)pyridin-2-yl)-2,3-dihydro-1H-inden-1-yl)oxy)phenyl)hex-4-ynoic acid methyl ester through the same procedure as used in Example 1. MS ESI (positive) m/z: 502.20 (M+H).
$^1$H NMR (400 MHz, CDCl$_3$) δ 8.36 (s, 1H), 7.66 (dd, J=8.6, 2.6 Hz, 1H), 7.46 (d, J=4.0 Hz, 1H), 7.31 (d, J=2.0 Hz, 2H), 7.25-7.23 (m, 1H), 7.03 (t, J=8.6 Hz, 1H), 6.96 (t, J=2.6 Hz, 2H), 5.92-5.90 (m, 1H), 5.01-4.99 (m, 1H), 4.06-3.93 (m, 5H), 3.61-3.57 (m, 1H), 3.38-3.19 (m, 1H), 2.80-2.77 (m, 1H), 2.76-2.74 (m, 1H), 2.65-2.39 (m, 4H), 1.54 (s, 3H).

Example 12

(S)-3-(4-(((R)-7-Fluoro-4-(4-methyl-6-((3-methyloxetan-3-yl)methoxy)pyridin-3-yl)-2,3-dihydro-1H-inden-1-yl)oxy)phenyl)hex-4-ynoic acid The title compound was synthesized from (S)-3-(4-(((R)-7-fluoro-4-(4-methyl-6-((3-methyloxetan-3-yl)methoxy)pyridin-3-yl)-2,3-dihydro-1H-inden-1-yl)oxy)phenyl)hex-4-ynoic acid methyl ester through the same procedure as used in Example 1. MS ESI (positive) m/z: 530.17 (M+H).
$^1$H NMR (400 MHz, CDCl$_3$) δ 7.91 (s, 1H), 7.32-7.30 (m, 2H), 7.15-7.12 (m, 1H), 7.02-7.00 (m, 1H), 6.98-6.94 (m, 2H), 6.77 (s, 1H), 5.95-5.93 (m, 1H), 4.68 (d, J=5.6 Hz, 2H), 4.46 (d, J=5.6 Hz, 2H), 4.38 (s, 2H), 4.09-4.08 (m, 1H), 3.03-2.90 (m, 1H), 2.78-2.65 (m, 3H), 2.43-2.37 (m, 1H), 2.32-2.27 (m, 1H), 2.10 (s, 3H), 1.83 (d, J=2.4 Hz, 3H).

Example 13

(S)-3-(4-(((R)-7-Fluoro-4-(2-methyl-6-((3-methyloxetan-3-yl)methoxy)pyridin-3-yl)-2,3-dihydro-1H-inden-1-yl)oxy)phenyl)hex-4-ynoic acid The title compound was synthesized from (S)-3-(4-(((R)-7-fluoro-4-(2-methyl-6-((3-methyloxetan-3-yl)methoxy)pyridin-3-yl)-2,3-dihydro-1H-inden-1-yl)oxy)phenyl)hex-4-ynoic acid methyl ester through the same procedure as used in Example 1. MS ESI (positive) m/z: 530.16 (M+H).
$^1$H NMR (400 MHz, CDCl$_3$) δ 7.38-7.29 (m, 3H), 7.16-7.08 (m, 1H), 7.00-6.90 (m, 3H), 6.64 (d, J=8.4 Hz, 1H), 5.91 (d, J=5.2 Hz, 1H), 4.69 (d, J=5.8 Hz, 2H), 4.46 (d, J=5.8 Hz, 2H), 4.40 (s, 2H), 4.12-4.05 (m, 1H), 2.99-2.88 (m, 1H), 2.85-2.64 (m, 2H), 2.62-2.54 (m, 1H), 2.48-2.31 (m, 1H), 2.29-2.20 (m, 4H), 1.81 (d, J=2.4 Hz, 3H).

Example 14

(S)-3-(4-(((R)-7-Fluoro-4-(5-((3)-methyloxetan-3-yl)methoxy)pyridin-2-yl)-2,3-dihydro-1H-inden-1-yl)oxy)phenyl)hex-4-ynoic acid The title compound was synthesized from (S)-3-(4-(((R)-7-fluoro-4-(5-((3-methyloxetan-3-yl)methoxy)pyridin-2-yl)-2,3-dihydro-1H-inden-1-yl)oxy)phenyl)hex-4-ynoic acid methyl ester through the same procedure as used in Example 1. MS ESI (positive) m/z: 516.13 (M+H).
$^1$H NMR (400 MHz, CDCl$_3$) δ 8.45 (d, J=2.8 Hz, 1H), 7.65-7.60 (m, 1H), 7.49 (d, J=8.4 Hz, 1H), 7.37 (dd, J=8.4, 2.4 Hz, 1H), 7.32 (d, J=8.8 Hz, 2H), 7.05 (t, J=8.4 Hz, 1H), 6.94 (d, J=8.4 Hz, 2H), 5.93-5.90 (m, 1H), 4.58 (dd, J=58.2, 6.2 Hz, 4H), 4.15 (s, 3H), 4.11-4.02 (m, 1H), 3.37-3.28 (m, 1H), 3.12-3.02 (m, 1H), 2.86-2.69 (m, 2H), 2.44-2.35 (m, 2H), 1.88-1.82 (m, 3H), 1.48 (s, 3H).

Example 15

(S)-3-(4-(((R)-7-Fluoro-4-(5-(((R)-tetrahydrofuran-3-yl)oxy)pyridin-3-yl)-2,3-dihydro-1H-inden-1-yl)oxy)phenyl)hex-4-ynoic acid The title compound was synthesized from (S)-3-(4-(((R)-7-fluoro-4-(5-(((R)-tetrahydrofuran-3-yl)oxy)pyridin-3-yl)-2,3-dihydro-1H-inden-1-yl)oxy)phenyl)hex-4-ynoic acid methyl ester through the same procedure as used in Example 1. MS ESI (positive) m/z: 502.19 (M+H).
$^1$H NMR (400 MHz, CDCl$_3$) δ 8.38-8.15 (br S, 2H), 7.37-7.30 (m, 4H), 7.07 (t, J=8.4 Hz, 1H), 6.91 (d, J=8.4 Hz, 2H), 5.92 (t, J=4.0 Hz, 1H), 5.08-4.99 (m, 1H), 4.14-3.98 (m, 4H), 3.97-3.91 (m, 1H), 3.22-3.13 (m, 1H), 2.90-2.71 (m, 3H), 2.41-2.37 (m, 2H), 2.34-2.23 (m, 1H), 2.21-2.15 (m, 1H), 1.84 (d, J=2.4 Hz, 3H).

Example 16

(S)-3-(4-(((R)-7-Fluoro-4-(5-((tetrahydro-2H-pyran-4-yl)oxy)pyridin-3-yl)-2,3-dihydro-1H-inden-1-yl)oxy)phenyl)hex-4-ynoic acid The title compound was synthesized from (S)-3-(4-(((R)-7-fluoro-4-(5-((tetrahydro-2H-pyran-4-yl)oxy)pyridin-3-yl)-2,3-dihydro-1H-inden-1-yl)oxy)phenyl)hex-4-ynoic acid methyl ester through the same procedure as used in Example 1. MS ESI (positive) m/z: 516.16 (M+H).
$^1$H NMR (400 MHz, CDCl$_3$) δ 8.30 J=2.4 Hz, 1H), 8.24 (s, 1H), 7.35-7.30 (m, 3H), 7.05 (t, J=8.4 Hz, 1H), 6.94 (d, J=8.4 Hz, 2H), 5.92-5.90 (m, 1H), 4.59-4.55 (m, 1H), 4.11-4.06 (m, 1H), 4.02-3.97 (m, 2H), 3.63-3.57 (m, 2H), 3.27-3.19 (m, 1H), 2.89-2.81 (m, 2H), 2.76-2.70 (m, 1H), 2.39-2.34 (m, 2H), 2.08-2.01 (m, 2H), 1.87-1.80 (m, 5H).

Example 17

(S)-3-(4-(((R)-4-(5-Chloro-6-((tetrahydro-2H-pyran-4-yl)oxy)pyridin-3-yl)-7-fluoro-2,3-dihydro-1H-inden-1-yl)oxy)phenyl)hex-4-ynoic acid The title compound was synthesized from (S)-3-(4-(((R)-4-(5-chloro-6-((tetrahydro-2H-pyran-4-yl)oxy)pyridin-3-yl)-7-fluoro-2,3-dihydro-1H-inden-1-yl)oxy)phenyl)hex-4-ynoic acid methyl ester through the same procedure as used in Example 1. MS ESI (positive) m/z: 550.06 (M+H).
$^1$H NMR (400 MHz, CDCl$_3$) δ 8.05 (d, J=2.4 Hz, 1H), 7.71 (d, J=2.0 Hz, 1H), 7.34 (d, J=4.8 Hz, 2H), 7.30-7.26 (m, 1H), 7.03 (t, J=8.4 Hz, 1H), 6.95 (d, J=8.4 Hz, 2H), 5.93-5.89 (m, 1H), 5.40-5.32 (m, 1H), 4.10-4.00 (m, 3H), 3.70-3.63 (m, 2H), 3.31-3.20 (m, 1H), 2.91-2.70 (m, 3H), 2.45-2.32 (m, 2H), 2.15-2.06 (m, 2H), 1.95-1.80 (m, 5H).

Example 18

(S)-3-(4-(((R)-4-(5-Cyano-6-(((R)-tetrahydrofuran-3-yl)oxy)pyridin-3-yl)-7-fluoro-2,3-dihydro-1H-inden-1-yl)oxy)phenyl)hex-4-ynoic acid The title compound was synthesized from (S)-3-(4-(((R)-4-(5-cyano-6-(((R)-tetrahydrofuran-3-yl)oxy)pyridin-3-yl)-

7-fluoro-2,3-dihydro-1H-inden-1-yl)oxy)phenyl)hex-4-ynoic acid methyl ester through the same procedure as used in Example 1. MS ESI (positive) m/z: 527.04 (M+H).

¹H NMR (400 MHz, CDCl₃) δ 8.37 (d, J=2.4 Hz, 1H), 7.93 (d, J=2.4 Hz, 1H), 7.34 (d, J=8.8 Hz, 2H), 7.30-7.26 (m, 1H), 7.06 (t, J=8.4 Hz, 1H), 6.96 (d, J=8.4 Hz, 2H), 5.93-5.90 (m, 1H), 5.67-5.63 (m, 1H), 4.17-3.92 (m, 5H), 3.31-3.20 (m, 1H), 2.90-2.71 (m, 3H), 2.45-2.25 (m, 4H), 1.84 (d, J=2.4 Hz, 3H).

Example 19

(S)-3-(4-(((R)-4-(5-Cyano-6-((tetrahydro-2H-pyran-4-yl)oxy)pyridin-3-yl)-7-fluoro-2,3-dihydro-1H-inden-1-yl)oxy)phenyl)hex-4-ynoic acid The title compound was synthesized from (S)-3-(4-(((R)-4-(5-cyano-6-((tetrahydro-2H-pyran-4-yl)oxy)pyridin-3-yl)-7-fluoro-2,3-dihydro-1H-inden-1-yl)oxy)phenyl)hex-4-ynoic acid methyl ester through the same procedure as used in Example 1. MS ESI (positive) m/z: 540.93 (M+H).

¹H NMR (400 MHz, CDCl₃) δ 8.36 (d, J=2.4 Hz, 1H), 7.93 (d, J=2.4 Hz, 1H), 7.34 (d, J=8.8 Hz, 2H), 7.29-7.26 (m, 1H), 7.06 (t, J=8.4 Hz, 1H), 6.96 (d, J=8.8 Hz, 2H), 5.93-5.91 (m, 1H), 5.41-5.39 (m, 1H), 4.08-4.01 (m, 3H), 3.68-3.62 (m, 2H), 3.29-3.21 (m, 1H), 2.88-2.80 (m, 2H), 2.76-2.71 (m, 1H), 2.40-2.37 (m, 2H), 3.13-2.09 (m, 2H), 1.93-1.89 (m, 2H), 1.85 (d, J=2.4 Hz, 3H).

Example 20

(S)-3-(4-(((R)-5-Cyano-4-(6-(((R)-tetrahydrofuran-3-yl)oxy)pyridin-3-yl)-2,3-dihydro-1H-inden-1-yl)oxy)phenyl)hex-4-ynoic acid The title compound was synthesized from (S)-3-(4-(((R)-5-cyano-4-(6-(((R)-tetrahydrofuran-3-yl)oxy)pyridin-3-yl)-2,3-dihydro-1H-inden-1-yl)oxy)phenyl)hex-4-ynoic acid methyl ester through the same procedure as used in Example 1. MS ESI (positive) m/z: 509.12 (M+H).

¹H NMR (400 MHz, CDCl₃) δ 8.19 (d, J=2.4 Hz, 1H), 7.89-7.64 (m, 2H), 7.50 (d, J=8.0 Hz, 1H), 7.35 (d, J=8.8 Hz, 2H), 6.95 (d, J=8.4 Hz, 2H), 6.87 (d, J=8.4 Hz, 1H), 5.79 (t, J=5.8 Hz, 1H), 5.65-5.60 (m, 1H), 4.10-3.90 (m, 5H), 3.05-2.97 (m, 1H), 2.90-2.53 (m, 4H), 2.35-2.22 (m, 3H), 1.83 (d, J=2.0 Hz, 3H).

Example 21

(S)-3-(4-(((R)-5-Fluoro-4-(6-(((R)-tetrahydrofuran-3-yl)oxy)pyridin-3-yl)-2,3-dihydro-1H-inden-1-yl)oxy)phenyl)hex-4-ynoic acid The title compound was synthesized from (S)-3-(4-(((R)-5-fluoro-4-(6-(((R)-tetrahydrofuran-3-yl)oxy)pyridin-3-yl)-2,3-dihydro-1H-inden-1-yl)oxy)phenyl)hex-4-ynoic acid methyl ester through the same procedure as used in Example 1. MS ESI (positive) m/z: 502.22 (M+H).

¹H NMR (400 MHz, CDCl₃) δ 8.14 (d, J=2.4 Hz, 1H), 7.64 (d, J=8.6 Hz, 1H), 7.50 (d, J=8.0 Hz, 1H), 7.47 (d, J=8.8 Hz, 2H), 7.08 (t, J=8.4 Hz, 1H), 6.94 (d, J=8.4 Hz, 2H), 6.84 (d, J=4.4 Hz, 1H), 5.79 (t, J=5.8 Hz, 1H), 5.65-5.60 (m, 1H), 4.10-3.90 (m, 5H), 3.05-2.97 (m, 1H), 2.87-2.72 (m, 3H), 2.56-2.53 (m, 1H), 2.35-2.22 (m, 3H), 1.84 (d, J=2.0 Hz, 3H).

Example 22

(S)-3-(4-(((R)-5-Methoxy-4-(6-(((R)-tetrahydrofuran-3-yl)oxy)pyridin-3-yl)-2,3-dihydro-1H-inden-1-yl)oxy)phenyl)hex-4-ynoic acid The title compound was synthesized from (S)-3-(4-(((R)-5-methoxy-4-(6-(((R)-tetrahydrofuran-3-yl)oxy)pyridin-3-yl)-2,3-dihydro-1H-inden-1-yl)oxy)phenyl)hex-4-ynoic acid methyl ester through the same procedure as used in Example 1. MS ESI (positive) m/z: 514.16 (M+H).

¹H NMR (400 MHz, CDCl₃) δ 8.11 (d, J=2.4 Hz, 1H), 7.59 (dd, J=8.4, 2.4 Hz, 1H), 7.39 (d, J=8.4 Hz, 1H), 7.32 (d, J=8.4 Hz, 2H), 6.94 (d, J=8.4 Hz, 2H), 6.90 (d, J=8.4 Hz, 1H), 6.79 (d, J=8.4 Hz, 1H), 5.75-5.69 (m, 1H), 5.62-5.57 (m, 1H), 4.12-3.96 (m, 4H), 3.95-3.88 (m, 1H), 3.77 (s, 3H), 3.02-2.92 (m, 1H), 2.85-2.67 (m, 3H), 2.51-2.42 (m, 1H), 2.35-2.24 (m, 1H), 2.20-2.15 (m, 2H), 1.84 (d, J=2.4 Hz, 3H).

Example 23

(S)-3-(4-(((R)-5-Cyano-4-(6-((tetrahydro-2H-pyran-4-yl)oxy)pyridin-3-yl)-2,3-dihydro-1H-inden-1-yl)oxy)phenyl)hex-4-ynoic acid The title compound was synthesized from (S)-3-(4-(((R)-5-cyano-4-(6-((tetrahydro-2H-pyran-4-yl)oxy)pyridin-3-yl)-2,3-dihydro-1H-inden-1-yl)oxy)phenyl)hex-4-ynoic acid methyl ester through the same procedure as used in Example 1. MS ESI (positive) m/z: 523.09 (M+H).

¹H NMR (400 MHz, CDCl₃) δ 8.16 (d, J=2 Hz, 1H), 7.69-7.65 (m, 2H), 7.02 (t, J=8.6 Hz, 1H), 7.35 (d, J=8.4 Hz, 2H), 6.95 (d, J=8.4 Hz, 2H), 6.85 (d, J=8.6 Hz, 1H), 5.80-5.77 (m, 1H), 5.33-5.26 (m, 1H), 4.10-4.06 (m, 1H), 4.03-3.98 (m, 2H), 3.66-3.60 (m, 2H), 3.02-2.95 (m, 1H), 2.88-2.81 (m, 2H), 2.76-2.70 (m, 1H), 2.62-2.54 (m, 1H), 2.23-2.15 (m, 1H), 2.12-2.08 (m, 2H), 1.88-1.79 (m, 5H).

Example 24

(S)-3-(4-(((R)-5-Fluoro-4-(6-((tetrahydro-2H-pyran-4-yl)oxy)pyridin-3-yl)-2,3-dihydro-1H-inden-1-yl)oxy)phenyl)hex-4-ynoic acid The title compound was synthesized from (S)-3-(4-(((R)-5-fluoro-4-(6-((tetrahydro-2H-pyran-4-yl)oxy)pyridin-3-yl)-2,3-dihydro-1H-inden-1-yl)oxy)phenyl)hex-4-ynoic acid methyl ester through the same procedure as used in Example 1. MS ESI (positive) m/z: 516.17 (M+H).

¹H NMR (400 MHz, CDCl₃) δ 8.12 (d, J=2.4 Hz, 1H), 7.61 (d, J=8.6 Hz, 1H), 7.48 (d, J=8.0 Hz, 1H), 7.45 (d, J=8.8 Hz, 2H), 7.06 (t, J=8.4 Hz, 1H), 6.84 (d, J=8.4 Hz, 2H), 6.74 (d, J=4.4 Hz, 1H), 5.68 (t, J=5.8 Hz, 1H), 5.33-5.26 (m, 1H), 4.08-3.96 (m, 3H), 3.65-3.60 (m, 2H), 3.02-2.95 (m, 1H), 2.86-2.79 (m, 2H), 2.74-2.69 (m, 1H), 2.59-2.53 (m, 1H), 2.21-2.16 (m, 1H), 2.11-2.06 (m, 2H), 1.84-1.75 (m, 5H).

Example 25

(S)-3-(4-(((R)-5-Methoxy-4-(6-((tetrahydro-2H-pyran-4-yl)oxy)pyridin-3-yl)-2,3-dihydro-1H-inden-1-yl)oxy)phenyl)hex-4-ynoic acid The title compound was synthesized from (S)-3-(4-(((R)-5-methoxy-4-(6-((tetrahydro-2H-pyran-4-yl)oxy)pyridin-3-yl)-2,3-dihydro-1H-inden-1-yl)oxy)phenyl)hex-4-ynoic acid methyl ester through the same procedure as used in Example 1. MS ESI (positive) m/z: 528.16 (M+H).

¹H NMR (400 MHz, CDCl₃) δ 8.10 (d, J=2.4 Hz, 1H), 7.62 (dd, J=8.4, 2.4 Hz, 1H), 7.40 (d, J=8.4 Hz, 1H), 7.33 (d, J=8.4 Hz, 2H), 6.95 (d, J=8.4 Hz, 2H), 6.91 (d, J=8.4 Hz, 1H), 6.78 (d, J=8.4 Hz, 1H), 5.75-5.59 (m, 1H), 5.29-5.20 (m, 1H), 4.11-3.98 (m, 3H), 3.76 (s, 3H), 3.68-3.61 (m, 2H), 3.11-2.92 (m, 1H), 2.79-2.62 (m, 3H), 2.50-2.40 (m, 1H), 2.23-2.11 (m, 3H), 1.88-1.78 (m, 5H).

Example 26

(S)-3-(4-(((R)-7-Fluoro-4-(6-(((R)-tetrahydrofuran-3-yl)oxy)pyridin-3-yl)-2,3-dihydro-1H-inden-1-yl)amino)phenyl)hex-4-ynoic acid

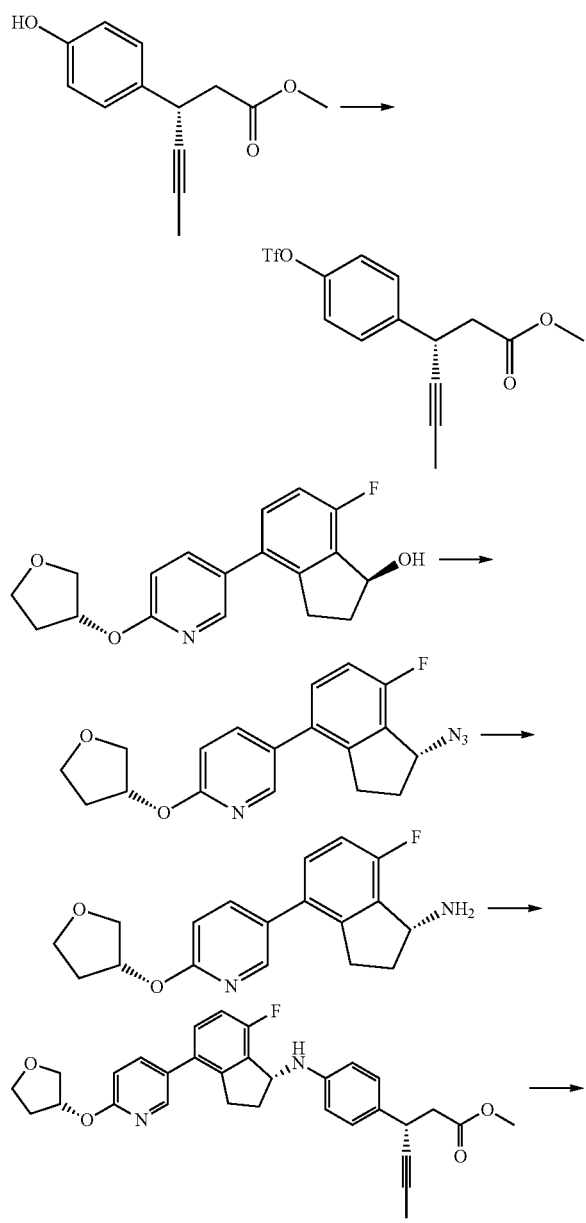

Step 1: (S)-3-(4-(((Trifluoromethyl)sulfonyl)oxy)phenyl)hex-4-ynoate methyl ester Trifluoromethanesulfonic anhydride (1.2 eq.) was added to a solution of triethylamine (3.0 eq.) and (3S)-3-(4-Hydroxy-phenyl)-hex-4-ynoic acid methyl ester (1.0 eq.) in dichloromethane (3.5 M). The reaction mixture was stirred at room temperature for 18 h. The mixture was diluted with dichloromethane and washed with saturated aqueous sodium bicarbonate solution. The organic layer was washed with brine and dried over magnesium sulfate, filtered and concentrated. The resultant residue was purified by flash column chromatography on silica gel to afford (S)-3-(4-(((trifluoromethyl)sulfonyl)oxy)phenyl)hex-4-ynoate methyl ester.

Step 2: 5-((R)-1-Azido-7-fluoro-2,3-dihydro-1H-inden-4-yl)-2-(((R)-tetrahydrofuran-3-yl)oxy)pyridine Diphenylphosphoryl azide (1.1 eq.) was added to a solution of (S)-7-fluoro-4-(6-(((R)-tetrahydrofuran-3-yl)oxy)pyridin-3-yl)-2,3-dihydro-1H-inden-1-ol (1.0 eq.) and 1,8-diazabicyclo(5.4.0)undec-7-ene (1.6 eq.) in toluene (0.2 M) at 4° C. The reaction mixture was stirred at room temperature for 18 h. The mixture was diluted with dichloromethane and washed with saturated aqueous sodium bicarbonate solution. The organic layer was washed with brine and dried over magnesium sulfate, filtered and concentrated. The resultant residue was purified by flash column chromatography on silica gel to afford 5-(((R)-1-azido-7-fluoro-2,3-dihydro-1H-inden-4-yl)-2-(((R)-tetrahydrofuran-3-yl)oxy)pyridine.

Step 3: (R)-7-Fluoro-4-(6-(((R)-tetrahydrofuran-3-yl)oxy)pyridin-3-yl)-2,3-dihydro-1H-inden-1-amine 5-((R)-1-Azido-7-fluoro-2,3-dihydro-1H-inden-4-yl)-2-(((R)-tetrahydrofuran-3-yl)oxy)pyridine (1.0 eq.) was added to a suspension of 10% palladium/charcoal (0.6 eq.) in ethanol (0.1 M). The mixture was stirred at room temperature for 2 h under H₂ atmosphere. The reaction mixture is filtered through Celite and concentrated. No further purification was needed to afford (R)-7-fluoro-4-(6-(((R)-tetrahydrofuran-3-yl)oxy)pyridin-3-yl)-2,3-dihydro-1H-inden-1-amine.

Step 4: (S)-3-(4-(((R)-7-Fluoro-4-(6-(((R)-tetrahydrofuran-3-yl)oxy)pyridin-3-yl)-2,3-dihydro-1H-inden-1-yl)amino)phenyl)hex-4-ynoic acid methyl ester Tris(dibenzylideneacetone)dipalladium(0) (0.05 eq.) was added to a solution of (R)-7-fluoro-4-(6-(((R)-tetrahydrofuran-3-yl)oxy)pyridin-3-yl)-2,3-dihydro-1H-inden-1- amine (1.0 eq.), (S)-3-(4-(((trifluoromethyl)sulfonyl)oxy)phenyl)hex-4-ynoate methyl ester (1.2 eq.), 2-dicyclohexylphosphino-2',4'',6'-triisopropylbiphenyl (0.2 eq.), and sodium tert-butoxide (2.5 eq.) in 1,4-dioxane (0.1 M). The reaction mixture was stirred at room temperature for 18 h. Then the mixture was reacted under microwave irradiation for 1 h. The reaction mixture was diluted with ethyl acetate and washed with water. The organic layer was washed with brine and dried over magnesium sulfate, filtered and concentrated. The resultant residue was purified by flash column chromatography on silica gel to afford (S)-3-(4-(((R)-7-fluoro-4-(6-(((R)-tetrahydrofuran-3-yl)oxy)pyridin-3-yl)-2,3-dihydro-1H-inden-1-yl)amino)phenyl)hex-4-ynoic acid methyl ester.

Step 5: (S)-3-(4-(((R)-7-Fluoro-4-(6-(((R)-tetrahydrofuran-3-yl)oxy)pyridin-3-yl)-2,3-dihydro-1H-inden-1-yl)amino)phenyl)hex-4-ynoic acid 2.0 M aqueous lithium hydroxide solution (5.0 eq.) was added to a solution of (S)-3-(4-(((R)-7-fluoro-4-(6-(((R)-tetrahydrofuran-3-yl)oxy)pyridin-3-yl)-2,3-dihydro-1H-inden-1-yl)amino)phenyl)hex-4-ynoic acid methyl ester (1.0 eq.) in tetrahydrofuran (1.0 M) and methanol (4.0 M) at 4° C. The reaction mixture was stirred at room temperature for 18 h. The mixture was neutralized with saturated aqueous ammonium chloride solution and diluted with ethyl acetate. The organic layer was washed with brine, dried over magnesium sulfate, filtered, and concentrated. The resultant residue was purified by flash column chromatography on silica gel to afford (S)-3-(4-(((R)-7-fluoro-4-(6-(((R)-tetrahydrofuran-3-yl)oxy)pyridin-3-yl)-2,3-dihydro-1H-inden-1-yl)amino)phenyl)hex-4-ynoic acid. MS ESI (positive) m/z: 501.15 (M+H).

$^1$H NMR (400 MHz, MeOD) δ 8.21 (d, J=2.0 Hz, 1H), 7.81 (dd, J=8.8, 2.4 Hz, 1H), 7.34-7.28 (m, 1H), 7.17 (d, J=8.4 Hz, 2H), 7.04 (t, J=8.8 Hz, 1H), 6.89 (d, J=8.8 Hz, 1H), 6.70 (d, J=8.4 Hz, 2H), 5.61-5.57 (m, 1H), 5.21-5.18 (m, 1H), 4.64 (br s, 1H), 4.09-3.89 (m, 5H), 3.29-3.20 (m, 1H), 2.91-2.82 (m, 1H), 2.67-2.60 (m, 2H), 2.40-2.28 (m, 2H), 2.22-2.12 (m, 2H), 1.83 (d, J=2.4 Hz, 3H).

Example 27

3-(6-(((R)-7-Fluoro-4-(6-(((R)-tetrahydrofuran-3-yl)oxy)pyridin-3-yl)-2,3-dihydro-1H-inden-1-yl)oxy)pyridin-3-yl)hex-4-ynoic acid

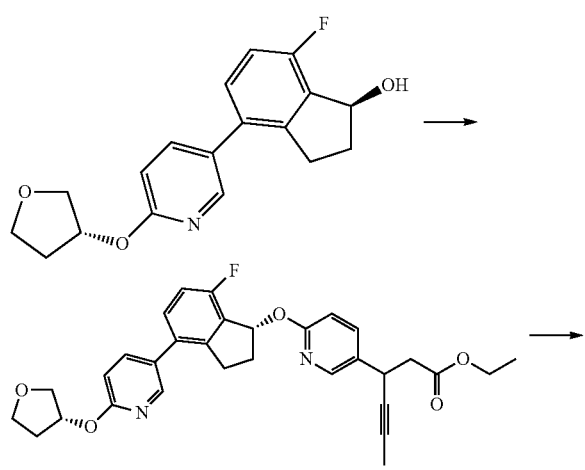

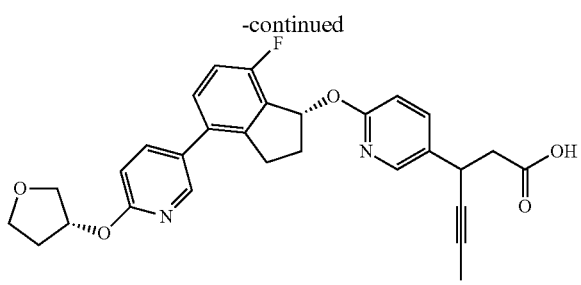

Step 1: 3-(6-(((R)-7-Fluoro-4-(6-(((R)-tetrahydrofuran-3-yl)oxy)pyridin-3-yl)-2,3-dihydro-1H-inden-1-yl)oxy)pyridin-3-yl)hex-4-ynoic acid ethyl ester 1,1'-(Azodicarbonyl)dipiperidine (1.5 eq.) was added portionwise over 10 min to a solution of (S)-7-fluoro-4-(6-(((R)-tetrahydrofuran-3-yl)oxy)pyridin-3-yl)-2,3-dihydro-1H-inden-1-ol (1.0 eq.), 3-(6-hydroxypyridin-3-yl)hex-4-ynoic acid ethyl ester (1.0 eq.), and tri-n-butylphosphine (1.5 eq.) in toluene (0.1 M) at 4° C. The reaction mixture was stirred at room temperature for 18 h. After addition of hexane (0.05 M) to the reaction mixture, the resulted white solid was removed by filtration. The filtrate was concentrated and then purified by flash column chromatography on silica gel to afford 3-(6-(((R)-7-fluoro-4-(6-(((R)-tetrahydrofuran-3-yl)oxy)pyridin-3-yl)-2,3-dihydro-1H-inden-1-yl)oxy)pyridin-3-yl)hex-4-ynoic acid methyl ester.

Step 2: 3-(6-(((R)-7-Fluoro-4-(6-(((R)-tetrahydrofuran-3-yl)oxy)pyridin-3-yl)-2,3-dihydro-1H-inden-1-yl)oxy)pyridin-3-yl)hex-4-ynoic acid 2.0 M aqueous lithium hydroxide solution (5.0 eq.) was added to a solution of 3-(6-(((R)-7-fluoro-4-(6-(((R)-tetrahydrofuran-3-yl)oxy)pyridin-3-yl)-2,3-dihydro-1H-inden-1-yl)oxy)pyridin-3-yl)hex-4-ynoic acid methyl ester (1.0 eq.) in tetrahydrofuran (1.0 M) and methanol (4.0 M) at 4° C. The reaction mixture was stirred at room temperature for 18 h. The mixture was neutralized with saturated aqueous ammonium chloride solution and diluted with ethyl acetate. The organic layer was washed with brine, dried over magnesium sulfate, filtered, and concentrated. The resultant residue was purified by flash column chromatography on silica gel to afford 3-(6-(((R)-7-fluoro-4-(6-(((R)-tetrahydrofuran-3-yl)oxy)pyridin-3-yl)-2,3-dihydro-1H-inden-1-yl)oxy)pyridin-3-yl)hex-4-ynoic acid. MS ESI (positive) m/z: 503.94 (M+H).

$^1$H NMR (400 MHz, CDCl$_3$) δ 8.16 (d, J=2.4 Hz, 1H), 8.12 (d, J=2.6 Hz, 1H), 7.57-7.54 (m, 2H), 7.27-7.25 (m, 1H), 6.94 (t, J=8.6 Hz, 1H), 6.66 (d, J=2.0 Hz, 1H), 6.63 (d, J=2.4, 0.4 Hz, 1H), 6.58-6.54 (m, 1H), 5.52-5.51 (m, 1H), 4.06-3.85 (m, 5H), 3.29-3.19 (m, 1H), 2.79-2.71 (m, 2H), 2.68-2.65 (m, 1H), 2.42-2.32 (m, 1H), 2.29-2.08 (m, 3H), 1.97 (d, J=2.4 Hz, 3H).

Comparative Example 1

[(3S)-6-{(2',6'-Dimethyl-4'-[3-(methylsulfonyl)propoxy]-[1,1'-biphenyl]-3-yl)}methoxy)-2,3-dihydro-1-benzofuran-3-yl]acetic acid

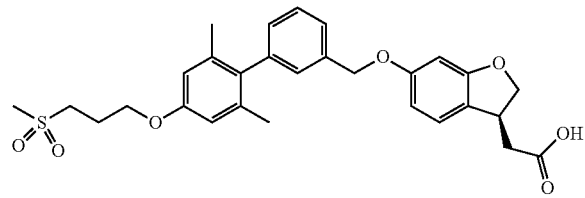 [SMILES: Cc1cc(OCCCS(C)(=O)=O)cc(C)c1-c1cccc(COc2ccc3c(c2)OC[C@H]3CC(=O)O)c1]

[(3S)-6-{(2',6'-Dimethyl-4'-[3-(methylsulfonyl)propoxy]-[1,1'-biphenyl]-3-yl)}methoxy)-2,3-dihydro-1-benzofuran-3-yl]acetic acid was synthesized based on the reference patent application No. 2008-001931.

In Vitro Evaluation

< in vitro Assay 1> Cell-Based Aequorin Assay

Recombinant cells grown 18 h prior to the test in media without antibiotics were detached by gentle flushing with PBS-EDTA (5 mM EDTA), recovered by centrifugation and resuspended in "assay buffer" (DMEM/HAM's F12 with HEPES+0.1% BSA fatty-acid free). Cells were incubated at room temperature for at least 4 h with Coelenterazine (Molecular Probes). Dose response curves with the reference compounds were performed before testing the compounds.

For agonistic activity testing, 50 µl of cell suspension was injected on 96-well plates with plated 50 µl of test compounds or reference agonist. The resulting emission of light was recorded using the Hamamatsu Functional Drug Screening System 6000 (FDSS 6000).

To standardize the emission of recorded light (determination of the "100% signal") across plates and across different experiments, some of the wells contained the reference agonist at its $EC_{100}$ obtained during the test validation. Agonistic activities of test compounds were expressed as a percentage of the activity of the reference agonist at its $EC_{100}$ concentration.

TABLE 1

| Example No. | Agonistic activity (%, 1 µM) |
| --- | --- |
| 1 | + |
| 3 | + |
| 5 | +++ |
| 6 | +++ |
| 7 | +++ |
| 8 | ++ |
| 15 | ++ |
| 16 | ++ |
| 17 | +++ |
| 18 | +++ |
| 19 | +++ |
| 20 | +++ |
| 21 | +++ |
| 24 | +++ |
| Comparative Example 1 | +++ |

Agonistic activities of compounds in the present invention are shown in Table 1. (+++: over 70, ++: 40-70, +: under 40)

As shown in Table 1, the example compounds of the present invention were confirmed to be excellent in activating GRP40 at 1 µM concentration. In particular, majority of the compounds exhibited more enhanced activities compared to the 'Comparative Example 1' which has been known to promote insulin secretion through the activation of GPR40.

INDUSTRIAL APPLICABILITY

The compounds of the present invention, as GPR40 agonists, are orally available and are extremely effective in lowering blood glucose level to normal state without any risk of inducing hypoglycemia via glucose-dependent insulin secretion. Therefore, compounds and/or therapeutically effective pharmaceutical composition comprising the compounds of the present invention are useful in the treatment, delaying, and/or regression of symptoms of type 2 diabetes.

In addition, compounds of the present invention modulate glucose excursion via GPR40 activation; the therapeutic effect can also be potentially available in obesity and hypertension.

In addition, since the compounds of the present invention have shown improved and/or enhanced therapeutic effects of alleviating and/or treating symptoms of type 2 diabetes compared to pre-existing medications when evaluated of glucose-lowering effects of the compounds on animal models and/or human-organ derived materials, the compounds can be evaluated as being highly useful to potential beneficiaries of the present invention.

The invention claimed is:

1. A compound represented by Formula (I), a racemate of the compound, an enantiomer of the compound, a diastereomer of the compound, or a pharmaceutically acceptable salt of the compound, the racemate, the enantiomer, or the diastereomer:

[Formula (I)]

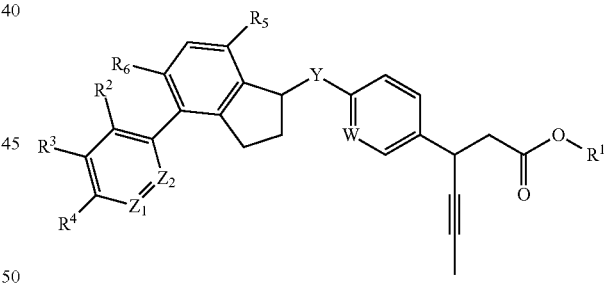

wherein $R^1$ is hydrogen, or $C_{1-4}$ linear or branched alkyl;
$R^2$ is hydrogen, cyano, hydroxyl, $C_{1-4}$ linear or branched alkyl, or $C_{1-4}$ linear or branched alkoxy;
$R^3$ is hydrogen, halogen, cyano, or $C_{1-4}$ linear or branched alkoxy when $R^4$ is $OR^8$; and
$R^4$ is hydrogen when $R^3$ is $OR^8$;
  wherein $R^8$ is $C_{3-10}$ heterocycloalkyl comprising 1-4 hetero atoms selected from the group consisting of N, O, and S, or alkyl substituted with $C_{3-10}$ heterocycloalkyl comprising 1-4 hetero atoms selected from the group consisting of N, O, and S;
$R^5$ and $R^6$ are each independently hydrogen, halogen, cyano, halomethyl, hydroxyl, $C_{1-4}$ linear or branched alkyl, or $C_{1-4}$ linear or branched alkoxy;
Y is NH or O;
$Z^1$ and $Z^2$ are each independently $CR^7$ or N;

wherein when $Z^1$ is N, $Z^2$ is $CR^7$, and when $Z^1$ is $CR^7$, $Z^2$ is N; and W is $CR^7$ or N;

wherein $R^7$ is hydrogen, halogen, cyano, hydroxyl, $C_{1-4}$ linear or branched alkyl, or $C_{1-4}$ linear or branched alkoxy.

2. The compound, the racemate, the enantiomer, the diastereomer, or the pharmaceutically acceptable salt according to claim 1, wherein:

$R^1$ is hydrogen, or $C_{1-4}$ linear or branched alkyl;

$R^2$ is hydrogen, or $C_{1-4}$ linear or branched alkyl;

$R^3$ is hydrogen, halogen, cyano, or $C_{1-4}$ linear alkoxy, when $R^4$ is,

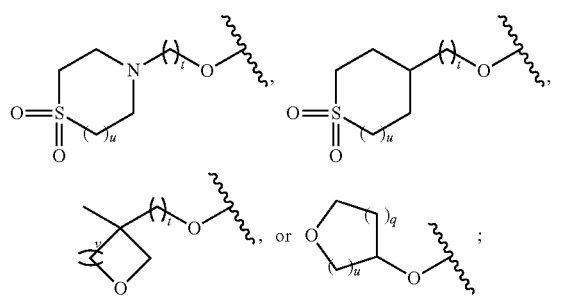

$R^4$ is hydrogen, when $R^3$ is

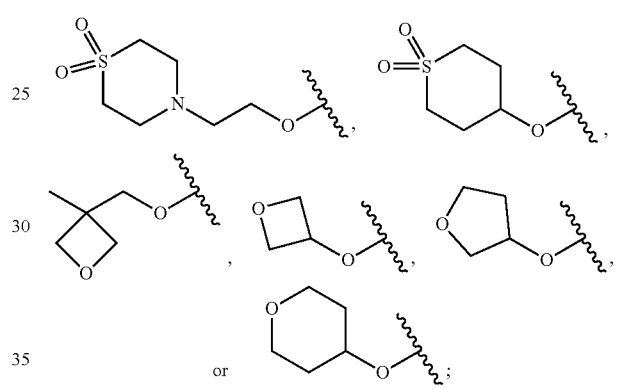

each occurrence of q is independently 0 or 1,
each occurrence of t is independently 0, 1, 2, or 3,
each occurrence of v is independently 1 or 2,
each occurrence of u is independently 1 or 2;

$R^5$ and $R^6$ are each independently hydrogen, halogen, cyano, or $C_{1-4}$ linear or branched alkoxy;

Y is NH or O;

$Z^1$ and $Z^2$ are each independently $CR^7$ or N;

wherein when $Z^1$ is N, $Z^2$ is $CR^7$, and when $Z^1$ is $CR^7$, $Z^2$ is N; and W is $CR^7$ or N;

wherein $R^7$ is hydrogen or $C_{1-2}$ linear alkyl.

3. The compound, the racemate, the enantiomer, the diastereomer, or the pharmaceutically acceptable salt according to claim 2, wherein:

$R^1$ is hydrogen;

$R^2$ is hydrogen or $C_{1-2}$ alkyl;

$R^3$ is hydrogen, chloro, cyano or $C_{1-2}$ alkoxy, when $R^4$ is

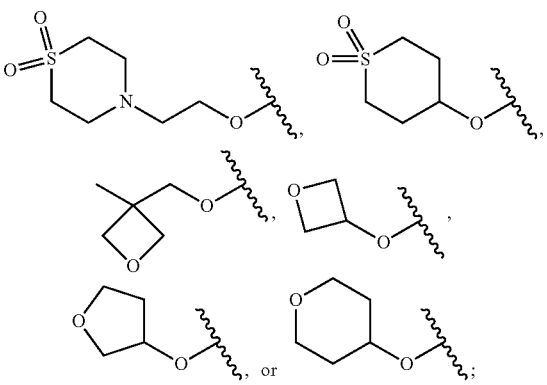

$R^4$ is hydrogen when $R^3$ is

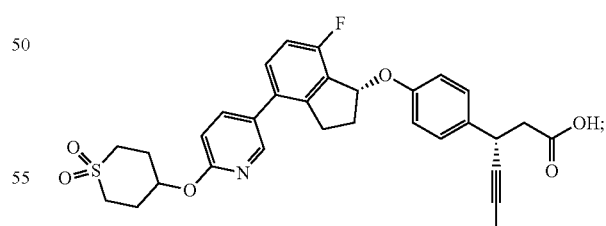

$R^5$ and $R^6$ are each independently hydrogen, fluoro, cyano, or $C_{1-2}$ linear alkoxy;

Y is NH or O;

$Z^1$ and $Z^2$ are each independently $CR^7$ or N, wherein when $Z^1$ is N, $Z^2$ is $CR^7$ and when $Z^1$ is $CR^7$, $Z^2$ is N; and W is $CR^7$ or N, wherein $R^7$ is hydrogen or $C_{1-2}$ linear alkyl.

4. A compound represented by at least one selected from the group consisting of:

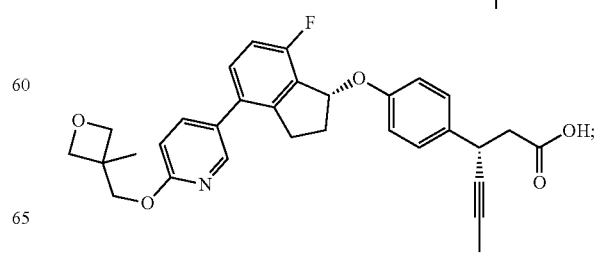

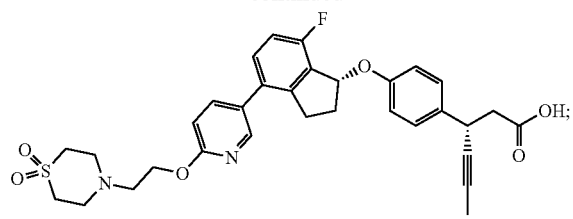
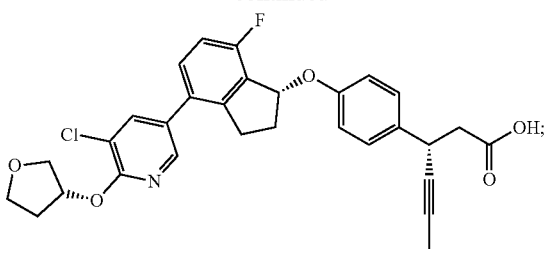

-continued

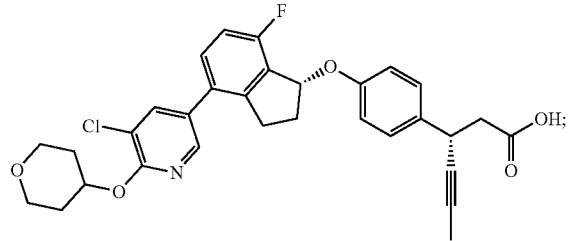

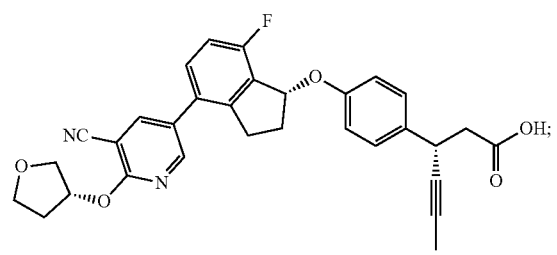

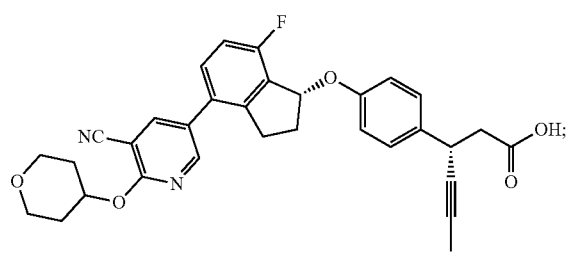

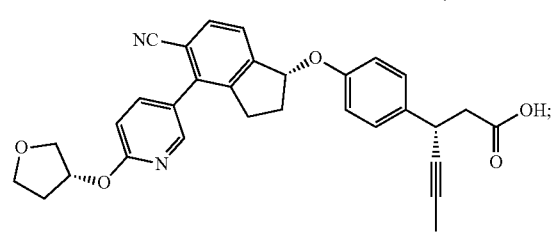

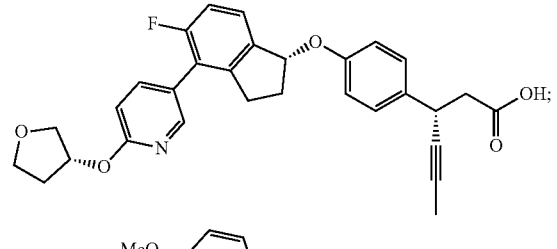

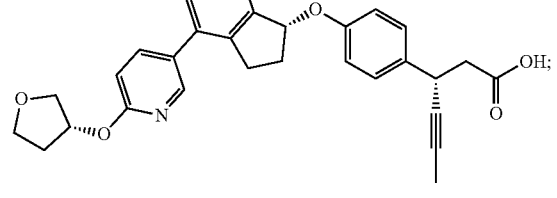

-continued

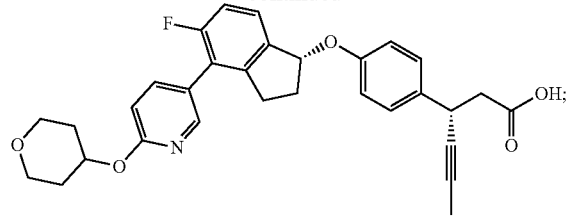

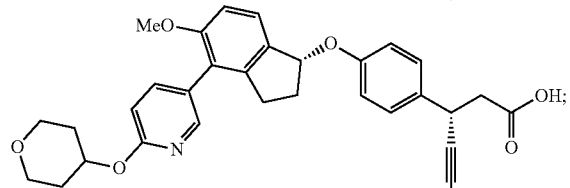

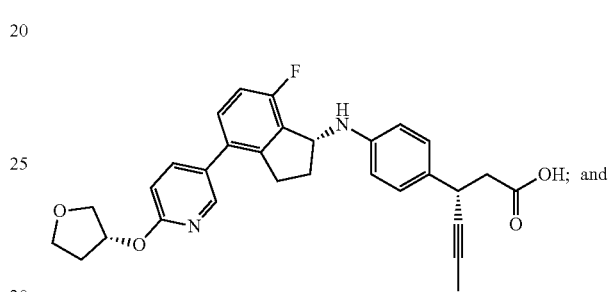

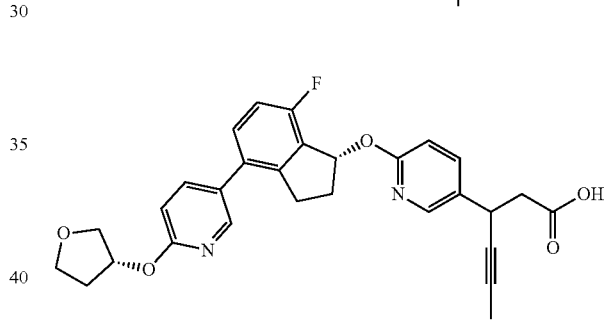

or a racemate of the compound, an enantiomer of the compound, a diastereomer of the compound, or a pharmaceutically acceptable salt of the compound, the racemate, the enantiomer, or the diastereomer.

5. A pharmaceutical composition for the treatment of metabolic disorder, comprising the compound, the racemate, the enantiomer, the diastereomer, or the pharmaceutically acceptable salt according to claim 1, wherein the metabolic disorder is selected from the group consisting of obesity, type 2 diabetes, incompatible glucose tolerance, insulin resistance, hyperglycemia, hyperlipidemia, hypertriglyceridemia, and hypercholesterolemia.

6. The pharmaceutical composition according to claim 5, further comprising a pharmaceutically acceptable excipient.

7. A method for treatment of metabolic disorder, comprising:
administering to a subject a pharmaceutical composition comprising a compound represented by Formula (I), a racemate of the compound, an enantiomer of the compound, a diastereomer of the compound, or a pharmaceutically acceptable salt of the compound, the racemate, the enantiomer, or the diastereomer:

[Formula (I)]

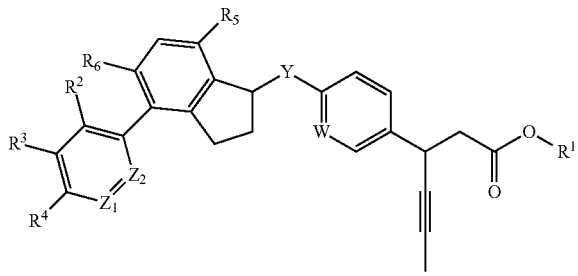

wherein $R^1$ is hydrogen, or $C_{1-4}$ linear or branched alkyl;
$R^2$ is hydrogen, cyano, hydroxyl, $C_{1-4}$ linear or branched alkyl, or $C_{1-4}$ linear or branched alkoxy;
$R^3$ is hydrogen, halogen, cyano, or $C_{1-4}$ linear or branched alkoxy when $R^4$ is $OR^8$
$R^4$ is hydrogen when $R^3$ is $OR^8$;
wherein $R^8$ is $C_{3-10}$ heterocycloalkyl comprising 1-4 hetero atoms selected from the group consisting of N, O, and S, or alkyl substituted with $C_{3-10}$ heterocycloalkyl comprising 1-4 hetero atoms selected from the group consisting of N, O, and S;
$R^5$ and $R^6$ are each independently hydrogen, halogen, cyano, halomethyl, hydroxyl, $C_{1-4}$ linear or branched alkyl, or $C_{1-4}$ linear or branched alkoxy;
Y is NH or O;
$Z^1$ and $Z^2$ are each independently $CR^7$ or N;
wherein when $Z^1$ is N, $Z^2$ is $CR^7$, and when $Z^1$ is $CR^7$, $Z^2$ is N; and
W is $CR^7$ or N;
wherein $R^7$ is hydrogen, halogen, cyano, hydroxyl, $C_{1-4}$ linear or branched alkyl, or $C_{1-4}$ linear or branched alkoxy; and
wherein the metabolic disorder is selected from the group consisting of obesity, type 2 diabetes, incompatible glucose tolerance, insulin resistance, hyperglycemia, hyperlipidemia, hypertriglyceridemia, and hypercholesterolemia.

8. A method of reducing a blood glucose level, increasing an activity of G-protein-coupled receptor 40 (GPR40), or a combination thereof in a subject in need thereof, wherein the method comprises administering to the subject an effective amount of a compound represented by Formula (I), a racemate of the compound, an enantiomer of the compound, a diastereomer of the compound, or a pharmaceutically acceptable salt of the compound, the racemate, the enantiomer, or the diastereomer:

[Formula (I)]

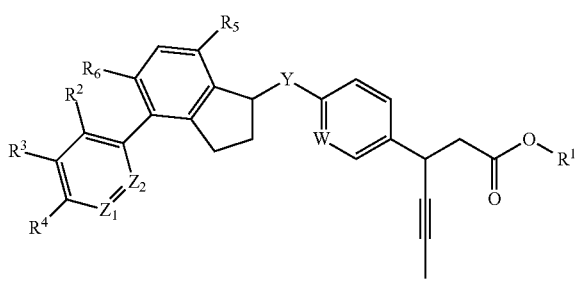

wherein $R^1$ is hydrogen, or $C_{1-4}$ linear or branched alkyl;
$R^2$ is hydrogen, cyano, hydroxyl, $C_{1-4}$ linear or branched alkyl, or $C_{1-4}$ linear or branched alkoxy;
$R^3$ is hydrogen, halogen, cyano, or $C_{1-4}$ linear or branched alkoxy when $R^4$ is $OR^8$
$R^4$ is hydrogen when $R^3$ is $OR^8$;
wherein $R^8$ is $C_{3-10}$ heterocycloalkyl comprising 1-4 hetero atoms selected from the group consisting of N, O, and S, or alkyl substituted with $C_{3-10}$ heterocycloalkyl comprising 1-4 hetero atoms selected from the group consisting of N, O, and S;
$R^5$ and $R^6$ are each independently hydrogen, halogen, cyano, halomethyl, hydroxyl, $C_{1-4}$ linear or branched alkyl, or $C_{1-4}$ linear or branched alkoxy;
Y is NH or O;
$Z^1$ and $Z^2$ are each independently $CR^7$ or N;
wherein when $Z^1$ is N, $Z^2$ is $CR^7$, and when $Z^1$ is $CR^7$, $Z^2$ is N; and
W is $CR^7$ or N;
wherein $R^7$ is hydrogen, halogen, cyano, hydroxyl, $C_{1-4}$ linear or branched alkyl, or $C_{1-4}$ linear or branched alkoxy.

9. The method of claim 8, wherein the subject has one or more metabolic disorders selected from the group consisting of obesity, type 2 diabetes, incompatible glucose tolerance, insulin resistance, hyperglycemia, hyperlipidemia, hypertriglyceridemia, and hypercholesterolemia.

10. A pharmaceutical composition for the treatment of metabolic disorder, comprising the compound, the racemate, the enantiomer, the diastereomer, or the pharmaceutically acceptable salt according to claim 2, wherein the metabolic disorder is selected from the group consisting of obesity, type 2 diabetes, incompatible glucose tolerance, insulin resistance, hyperglycemia, hyperlipidemia, hypertriglyceridemia, and hypercholesterolemia.

11. The pharmaceutical composition according to claim 10, further comprising a pharmaceutically acceptable excipient.

12. A pharmaceutical composition for the treatment of metabolic disorder, comprising the compound, the racemate, the enantiomer, the diastereomer, or the pharmaceutically acceptable salt according to claim 3, wherein the metabolic disorder is selected from the group consisting of obesity, type 2 diabetes, incompatible glucose tolerance, insulin resistance, hyperglycemia, hyperlipidemia, hypertriglyceridemia, and hypercholesterolemia.

13. The pharmaceutical composition according to claim 12, further comprising a pharmaceutically acceptable excipient.

14. A pharmaceutical composition for the treatment of metabolic disorder, comprising the compound, the racemate, the enantiomer, the diastereomer, or the pharmaceutically acceptable salt according to claim 4, wherein the metabolic disorder is selected from the group consisting of obesity, type 2 diabetes, incompatible glucose tolerance, insulin resistance, hyperglycemia, hyperlipidemia, hypertriglyceridemia, and hypercholesterolemia.

15. The pharmaceutical composition according to claim 14, further comprising a pharmaceutically acceptable excipient.

16. A method for treatment of metabolic disorder comprising: administering to a subject a pharmaceutical composition comprising a compound represented by at least one selected from the group consisting of:

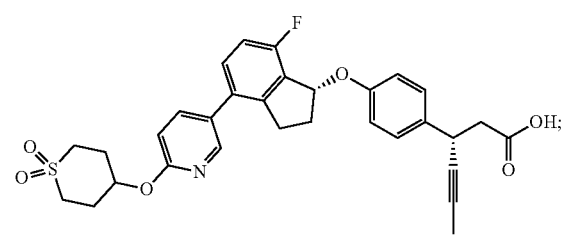
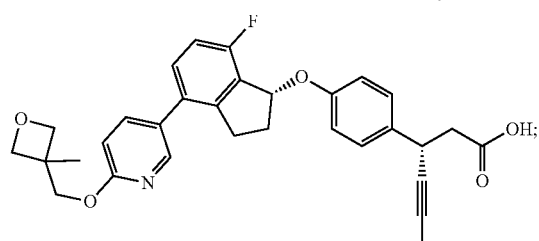
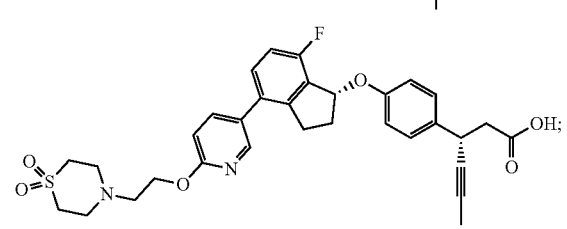
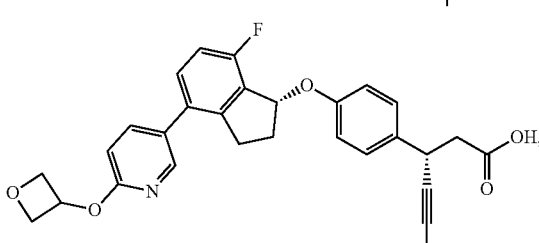
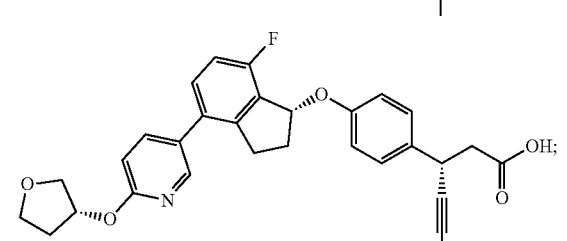
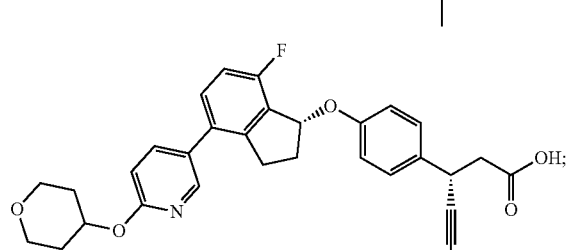
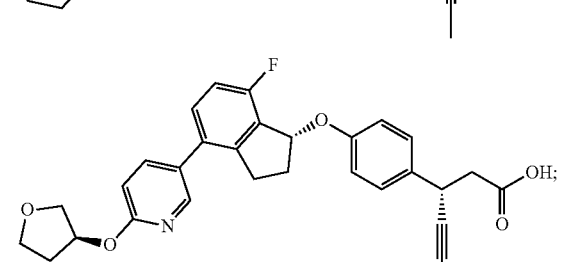
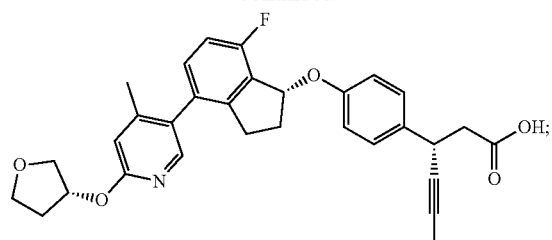
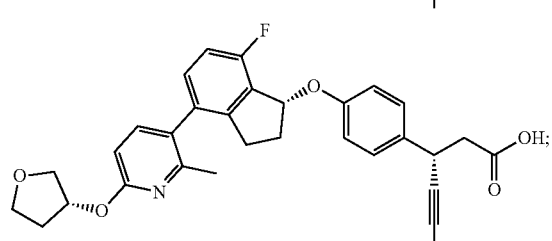
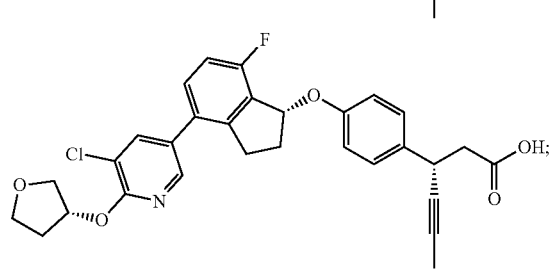
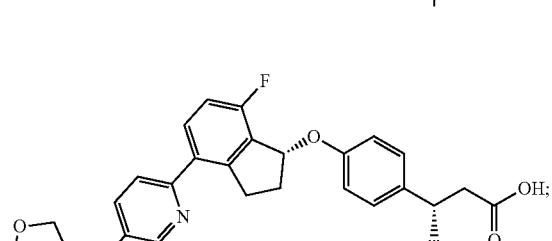
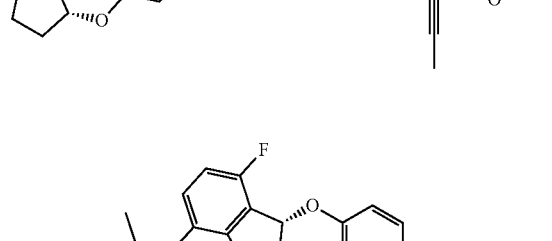
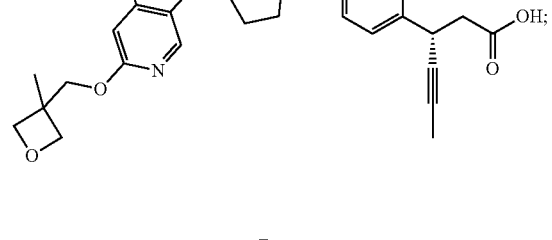
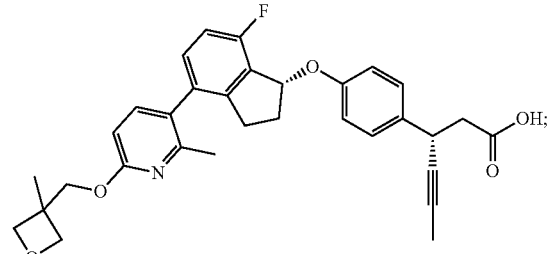

-continued

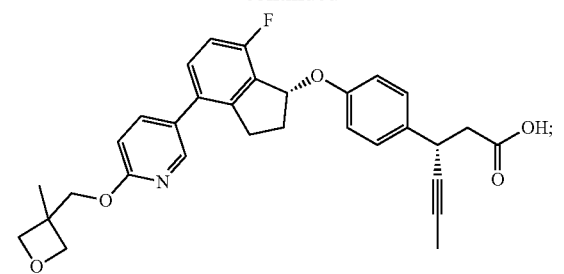
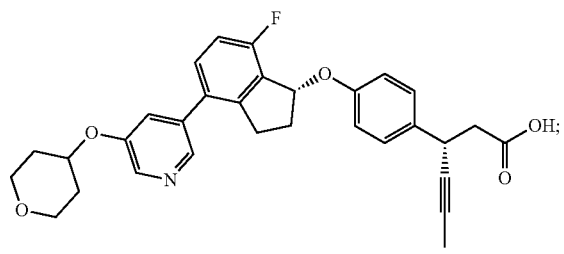
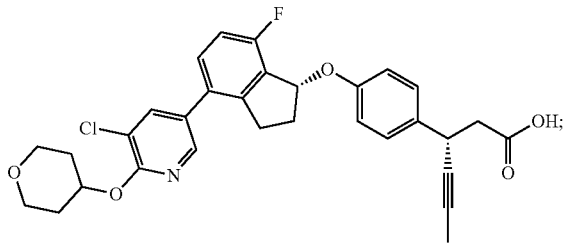
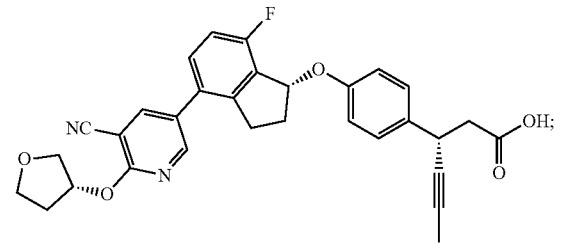
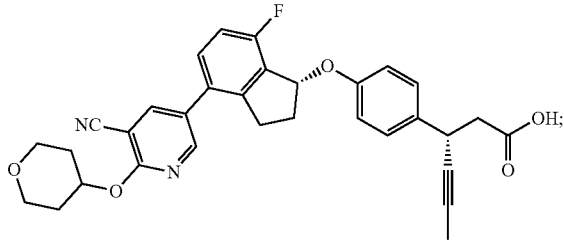
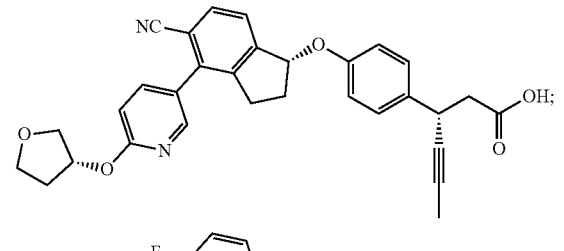
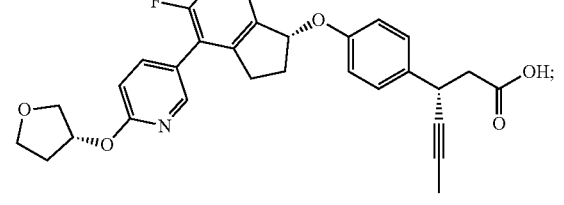

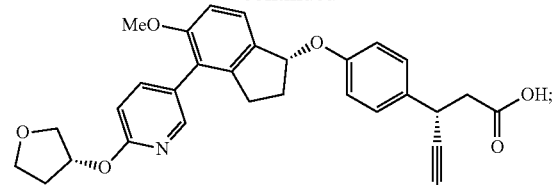
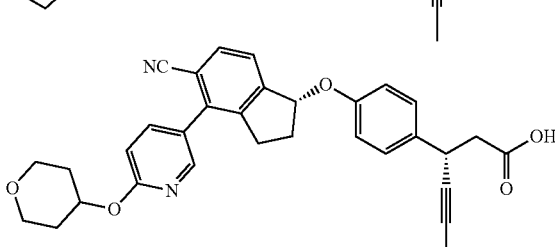
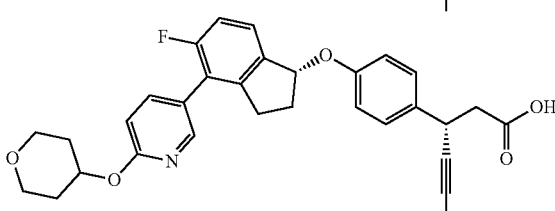
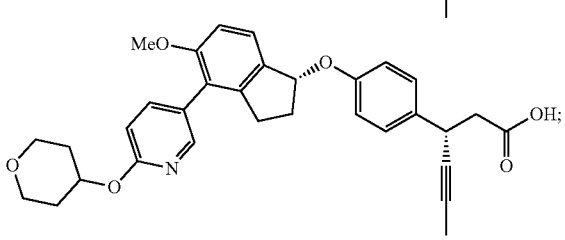
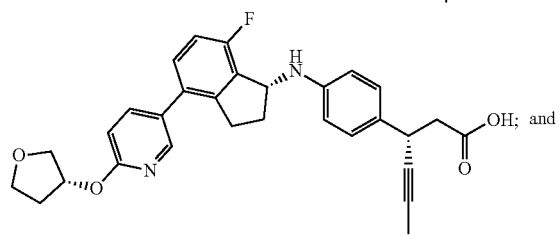
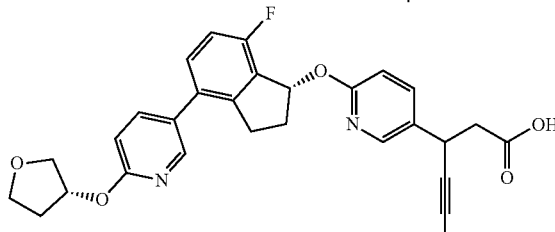
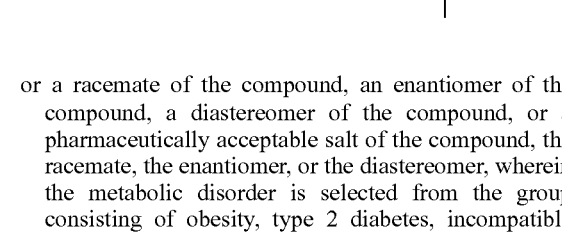
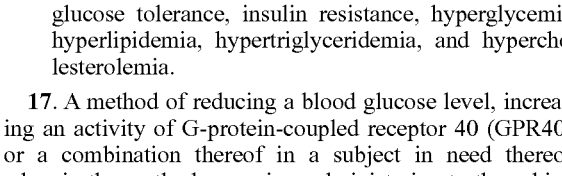

or a racemate of the compound, an enantiomer of the compound, a diastereomer of the compound, or a pharmaceutically acceptable salt of the compound, the racemate, the enantiomer, or the diastereomer, wherein the metabolic disorder is selected from the group consisting of obesity, type 2 diabetes, incompatible glucose tolerance, insulin resistance, hyperglycemia, hyperlipidemia, hypertriglyceridemia, and hypercholesterolemia.

17. A method of reducing a blood glucose level, increasing an activity of G-protein-coupled receptor 40 (GPR40), or a combination thereof in a subject in need thereof, wherein the method comprises administering to the subject an effective amount of a compound represented by at least one selected from the group consisting of:
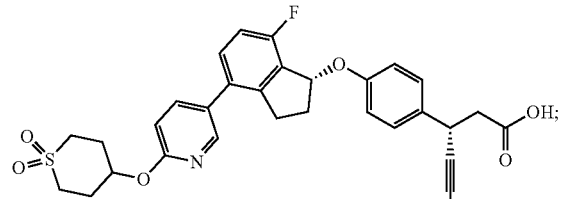
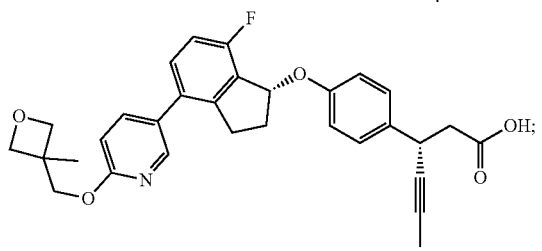
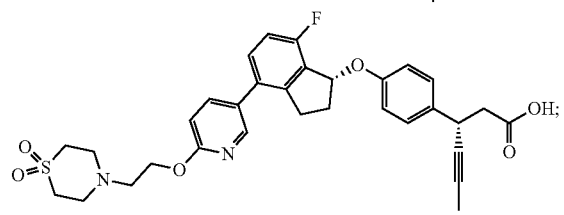
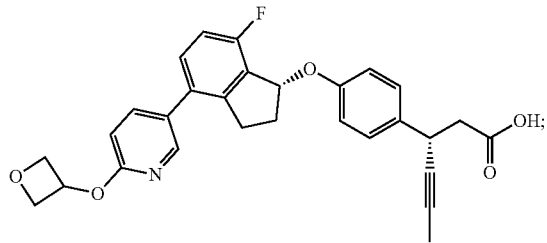
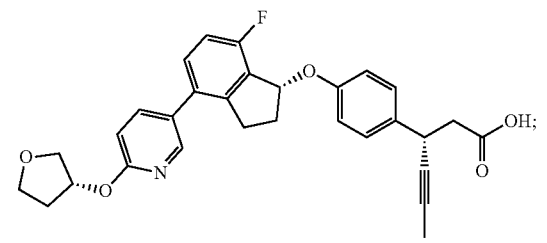
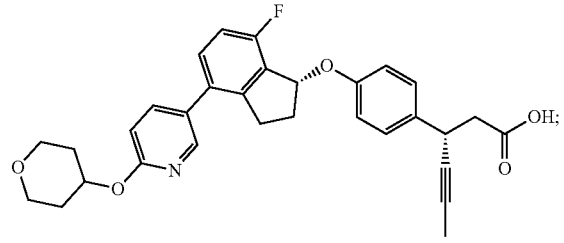
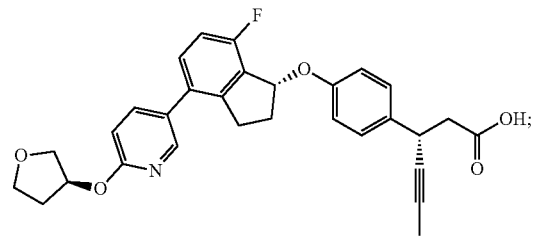
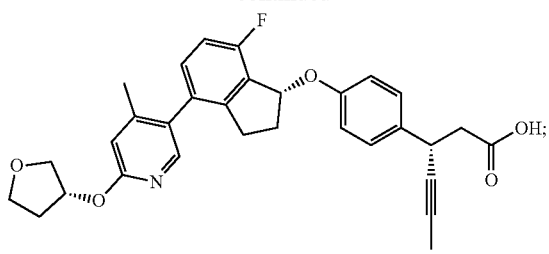
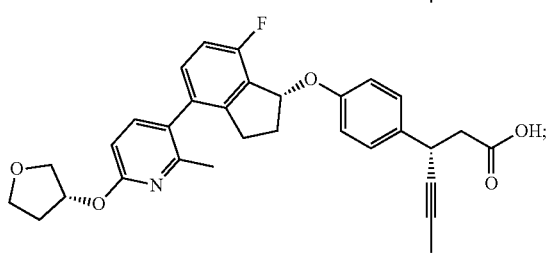
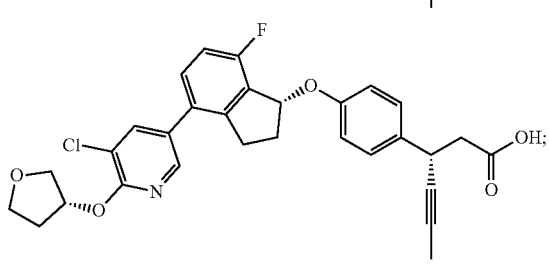
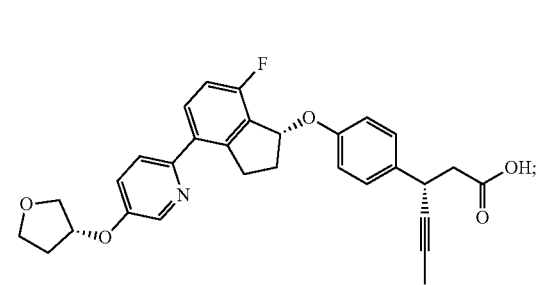
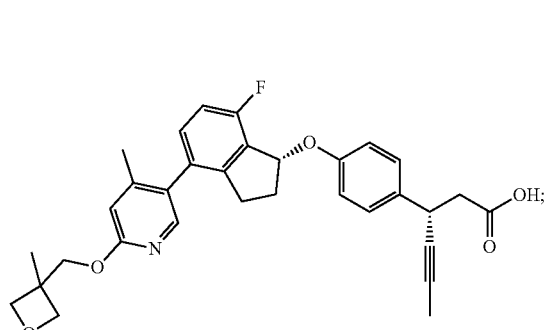
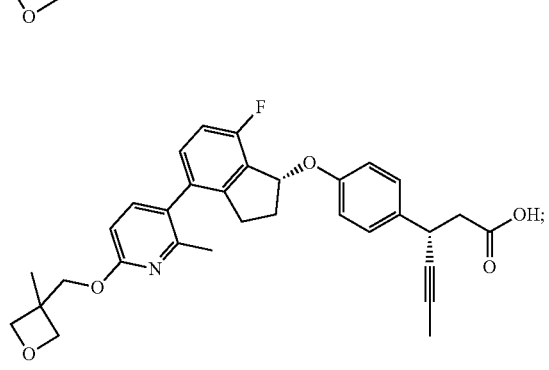

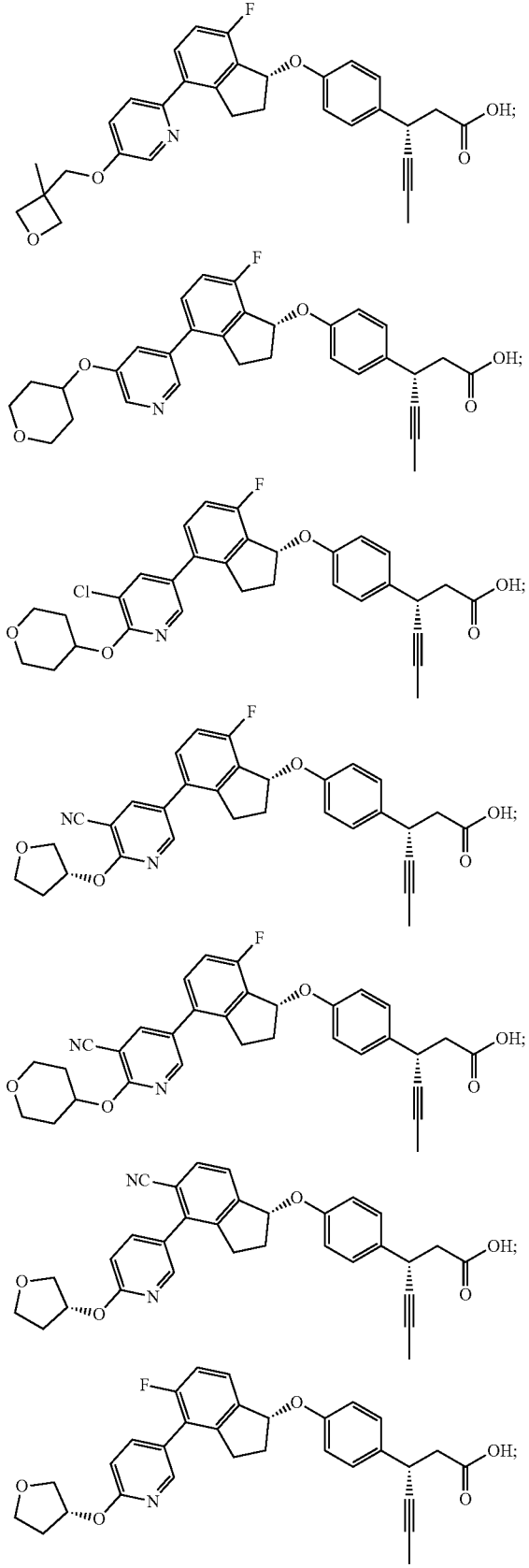
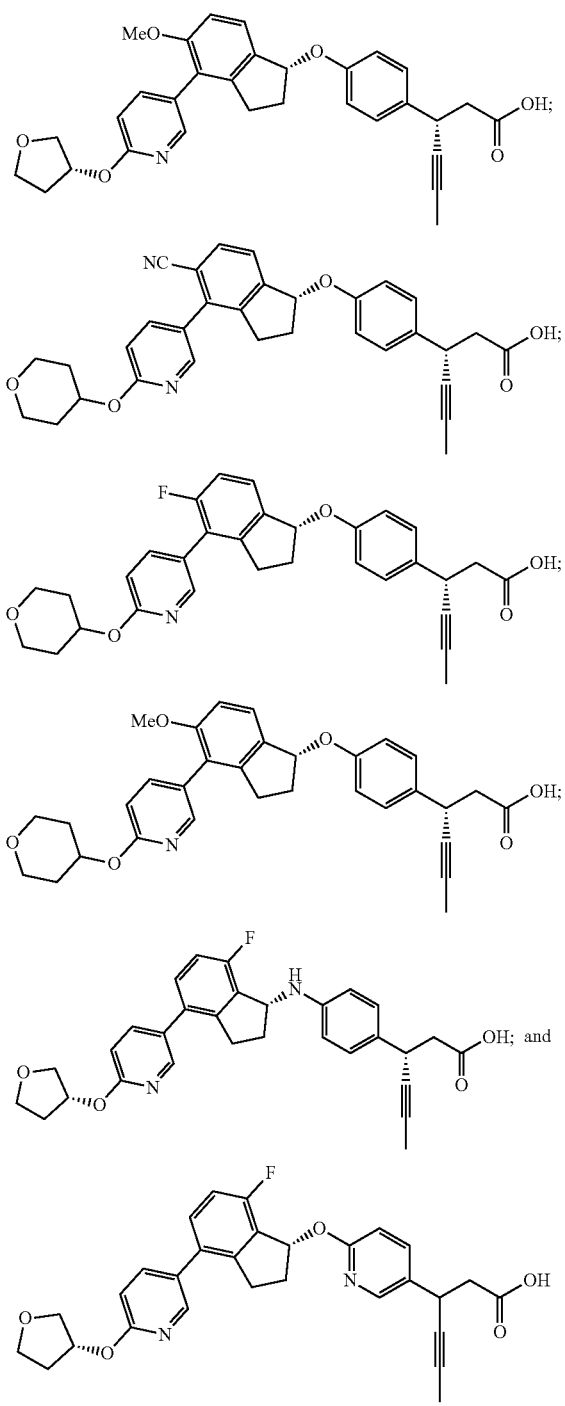
or a racemate of the compound, an enantiomer of the compound, a diastereomer of the compound, or a pharmaceutically acceptable salt of the compound, the racemate, the enantiomer, or the diastereomer.
* * * * *